(12) United States Patent
Yamasaki et al.

(10) Patent No.: US 8,282,883 B2
(45) Date of Patent: Oct. 9, 2012

(54) BLOWER TYPE CHEMICAL DIFFUSING APPARATUS WITH FUEL CELL POWER SUPPLY

(75) Inventors: Satoshi Yamasaki, Hatsukaichi (JP); Kazunori Yamamoto, Hatsukaichi (JP); Shinya Kawamura, Saeki-gun (JP); Yasuharu Takei, Hiroshima (JP); Takao Jo, Hiroshima (JP)

(73) Assignee: Fumakilla Limited, Tokyo (JP)

( * ) Notice: Subject to any disclaimer, the term of this patent is extended or adjusted under 35 U.S.C. 154(b) by 0 days.

(21) Appl. No.: 13/113,752

(22) Filed: May 23, 2011

(65) Prior Publication Data

US 2011/0221079 A1    Sep. 15, 2011

Related U.S. Application Data

(63) Continuation of application No. 11/632,099, filed as application No. PCT/JP2005/013521 on Jul. 15, 2005, now Pat. No. 8,025,845.

(30) Foreign Application Priority Data

| | | |
|---|---|---|
| Jul. 27, 2004 | (JP) | 2004-218352 |
| Aug. 10, 2004 | (JP) | 2004-232970 |
| Sep. 14, 2004 | (JP) | 2004-266200 |
| Dec. 7, 2004 | (JP) | 2004-353760 |
| Dec. 24, 2004 | (JP) | 2004-373417 |

(51) Int. Cl.
*A61L 9/03* (2006.01)

(52) U.S. Cl. .......................... 422/123; 422/124; 422/125

(58) Field of Classification Search .................. 422/123, 422/124, 125
See application file for complete search history.

(56) References Cited

U.S. PATENT DOCUMENTS

| | | | |
|---|---|---|---|
| 3,948,445 | A | 4/1976 | Andeweg |
| 4,059,422 | A | 11/1977 | Steiner |
| 4,301,095 | A | 11/1981 | Mettler et al. |
| 5,282,334 | A | 2/1994 | Kimura et al. |
| 5,657,926 | A | 8/1997 | Toda |
| 5,669,176 | A | 9/1997 | Miller |
| 6,789,421 | B2 | 9/2004 | Gore et al. |
| 7,141,320 | B2 | 11/2006 | Ito et al. |
| 2002/0062593 | A1 | 5/2002 | Matsunaga et al. |
| 2002/0094461 | A1 | 7/2002 | Skala et al. |
| 2002/0094462 | A1 | 7/2002 | Shioya et al. |

(Continued)

FOREIGN PATENT DOCUMENTS

EP    1 356 728 A1    10/2003

(Continued)

OTHER PUBLICATIONS

Notification Concerning Transmittal of International Preliminary Report on Patentability, Chapter I of the Patent Cooperation Treaty, dated Apr. 12, 2007, for PCT/JP2005/013521, 8 sheets.

(Continued)

*Primary Examiner* — Sean E Conley
(74) *Attorney, Agent, or Firm* — Holtz, Holtz, Goodman & Chick, PC

(57) ABSTRACT

A blower type chemical diffusing apparatus is disclosed which can be of service for an extended period of time and does not give rise to refuse disposal problems. The blower type chemical diffusing apparatus of the invention has an air blower, a chemical retainer and a fuel cell included in the apparatus body whereby powering the air blower to drive it with the fuel cell causes chemical from the chemical retainer to be emitted into an environmental atmosphere.

9 Claims, 22 Drawing Sheets

U.S. PATENT DOCUMENTS

| | | |
|---|---|---|
| 2003/0175171 A1 | 9/2003 | Yamamoto et al. |
| 2003/0192959 A1 | 10/2003 | Hess et al. |
| 2004/0197635 A1 | 10/2004 | Ito et al. |

FOREIGN PATENT DOCUMENTS

| | | |
|---|---|---|
| JP | 02-225403 A | 9/1990 |
| JP | 03-139236 A | 6/1991 |
| JP | 08-023851 A | 1/1996 |
| JP | 08-215308 A | 8/1996 |
| JP | 2001-103898 A | 4/2001 |
| JP | 2002-280035 A | 9/2002 |
| JP | 2002-281880 A | 10/2002 |
| JP | 2002-291392 A | 10/2002 |
| JP | 2004-105122 A | 4/2004 |
| JP | 2004-134355 A | 4/2004 |
| JP | 2004-147643 A | 5/2004 |
| JP | 2005-000111 A | 1/2005 |

OTHER PUBLICATIONS

Supplementary European Search Report (ESR) dated Sep. 26, 2007, issued in a counterpart European application.

International Search Report (ISR) mailed Oct. 25, 2005, issued in connection with International Application No. PCT/JP2005/013521.

BLOWER TYPE CHEMICAL DIFFUSING APPARATUS WITH FUEL CELL POWER SUPPLY

This application is a Continuation of U.S. application Ser. No. 11/632,099 filed Jan. 10, 2007 now U.S. Pat. No. 8,025,845, which application is a U.S. National Phase Application of International Application PCT/JP2005/013521 filed Jul. 15, 2005, the entire contents of both of which are incorporated herein by reference.

TECHNICAL FIELD

The present invention relates to a blower type chemical diffusing apparatus for volatilizing and diffusing a chemical such as an aromatic, deodorant, germicide, miticide, vermin or pest repellent, insecticide, or vermin growth retardant or sucking inhibitor, by the force of an airflow or wind generated by an air blower. More particularly, the invention relates to such a blower type chemical diffusing apparatus in which a power supply for driving a motor in the air flower is constituted with a fuel cell.

BACKGROUND ART

There is known a blower type chemical diffusing apparatus as disclosed in JP 2002-291392 A.

Such a blower type chemical diffusing apparatus is provided in its apparatus body with an air blower, a chemical receptacle and a power supply container wherein the air blower includes a fan and a motor, the chemical receptacle is stored with a volatile chemical and the power supply container contains a battery.

And, the motor is driven to rotate the fan, which causes air to flow through the chemical receptacle, which in turn volatilizes volatile chemical and diffuses it into an atmosphere.

The battery used in the conventional blower type chemical diffusing apparatus mentioned above is one or more of cells such as alkaline, manganese and lithium cells. Such cells have their limits in the period of service and when the service period is expired they are replaced with unused ones while being disposed of as refuse.

For this reason, they are economically disadvantageous and also entail the problem of refuse disposal.

As a result of zealous investigations on cells for the air blower in the blower type chemical diffusing apparatus mentioned above, the present inventors have noted that in recent years a small sized fuel cell is being developed using hydrogen as a fuel to be chemically reacted with oxygen in air to generate electric power. They have then found that using such a small sized fuel cell for the power supply of the air blower may realize a blower type chemical diffusing apparatus which is operable over an extended period of time while permitting the power supply therein to be recurrently used upon replenishment with fuel and which therefore is free of the refuse disposal problem hitherto encountered.

However, such a fuel cell when hydrogen is reacted with oxygen in air produces a water product which need be disposed of.

Thus, the conventional fuel cell, for example, requires a water reservoir to collect the water product. However, the need for such a water reservoir must raise the cost of the apparatus and increase its internal space.

There is also known a hot chemical volatilizer as disclosed in JP 2002-281880 A.

In the apparatus disclosed in that publication, a chemical mat impregnated with a chemical is placed on a heater in the apparatus main frame and an electric current is passed from an AC power supply through the heater to heat the same, thereby volatilizing chemical impregnated in the chemical mat into an atmosphere.

JP H02-225403 A discloses a hot chemical volatilizer of liquid chemical bottle type.

This volatilizer, in which a liquid absorbing wick or strip immersed in a liquid chemical within a bottle is heated indirectly by a ring shaped heater element to volatilize the liquid chemical, is a hot type chemical volatilizing devices that can be of service over an extended period of time.

These hot chemical volatilizing devices are generally large in power consumption for heating and, since they typically necessitate an AC power supply to energize the heater, the site of their use is limited to the inside of a house where the power supply is available, presenting the inconvenience that they cannot be used outdoors.

Using a battery instead of such an AC source as the heating power supply, a hot chemical volatilizing device of mat type and a hot chemical volatilizing device of liquid chemical bottle type are disclosed in JP H08-23851 A and JP 2000-103898 A, respectively. Such a device is advantageous in that it has no limitation in the site of it use and can be used outdoors and can be carried readily to anywhere as desired.

The apparatus, however, in which the number of battery cells used is more than small and their duration in service is relatively short, is not economical since they must very often be renewed. Let alone, these cells can hardly be its power supply if the apparatus requires heating at an elevated temperature.

Here again, such cells have their limits in the period of service and when the service period is expired they are replaced with unused ones while being disposed of as in refuse, presenting the problem of refuse disposal.

There is also known an ultrasonic chemical spraying apparatus in which a liquid chemical is ultrasonically atomized and sprayed as disclosed in JP H08-215308 A. This apparatus which unlike an aerosol device requires no spraying agent can be made smaller in size and is expected to a future chemical atomizer.

However, this apparatus generally requires a large power consumption for atomizing or spraying and, especially where a large amount of chemical is to be finely divided or atomized or spraying needs to be continued for an extended period of time, requires a larger number of battery cells used or reduces the cycle of cell exchanges and hence increases the number of cells to be exchanged or the times of cell exchanges. It is thus not only uneconomical but increases the amount of refuse.

DISCLOSURE OF THE INVENTION

It is an object of the present invention to provide a blower type chemical diffusing apparatus that uses a fuel cell whereby the apparatus is serviceable for an extended period of time, does not give rise to refuse disposal problems and not problems on safety either, has no limitation in the site of its use and can easily be carried to and used anywhere as desired.

It is also an object of the present invention to provide a blower type chemical diffusing apparatus that correlates a residual amount of fuel in a fuel tank in the fuel cell to an effective operating time period of the apparatus whereby consumables therein such as chemical or chemical retainer can be replenished or replaced at an appropriate time.

It is also an object of the present invention to provide a blower type chemical diffusing apparatus which can efficiently volatilize chemical by heating the chemical retainer with heat produced during the fuel cell's power generation, which can vaporize product water produced during the fuel cell's power generation by utilizing air flow produced by the air blower and which can readily be carried to and used anywhere as desired.

It is further an object of the present invention to provide a blower type chemical diffusing apparatus in which the air blower can be combined with a heat emitter or an ultrasonic generator to heat or atomize chemical for carrying the volatilized or atomized chemical by air flow by the air blower and thereby promote its volatilization from the chemical retainer and its diffusion into an environmental atmosphere efficiently.

There is provided in accordance with the present invention a blower type chemical diffusing apparatus, characterized by an air blower, a chemical retainer and a fuel cell included in an apparatus body whereby powering the air blower to drive it with the said fuel cell causes chemical from the chemical retainer to be emitted into an environmental atmosphere.

According to the feature of the invention mentioned above, powering a motor in the air blower with the fuel cell allows the motor in the air blower to continue to be driven for an extended period of time and hence the apparatus having the chemical retainer loaded with a plenty of chemical to continue to operate, while emitting chemical, over an extended period of time.

Also, with the fuel cell usable recurrently if refilled with fuel and hence needless to be disposed of as a refuse, the apparatus gives rise to no refuse disposal problem.

The present invention also provides a blower type chemical diffusing apparatus as set forth above, characterized in that the fuel cell comprises a cell body and a fuel tank and that the chemical retainer and the fuel tank are adapted to be supplied around the same time with chemical and fuel, respectively. It is also characterized in that the fuel cell comprises a cell body and a fuel tank and that the chemical retainer and the fuel tank are adapted to be concurrently mounted into and dismounted from the apparatus body.

According to such an apparatus makeup as mentioned above, a residual amount of fuel can be used as an indicator to replenish chemical and fuel around the same time. Also, with the chemical retainer and the fuel tank arranged to be concurrently mounted and concurrently dismounted, they can be exchanged at the same time.

The present invention also provides a blower type chemical diffusing apparatus as set forth above, characterized in that the fuel cell comprises a cell body and a fuel tank and that the apparatus body is provided with a see-through section through which an amount of fuel in the fuel tank can be visually checked.

According to the feature of the invention mentioned above in which there is provided a see-through section through which an amount of fuel in the fuel tank can be visually checked, correlating a residual amount of fuel in the fuel tank in the fuel cell to an effective operating time period of the apparatus allows visually ascertaining not only its operating end point but also the state of its use at any time and hence replenishing or replacing consumables therein such as chemical or chemical retainer at an appropriate time.

Further, visual checkability of a residual amount of fuel prevents its misperception and, with no time aging in connection therewith, gives precise information of an effective operating time period of the apparatus.

The present invention also provides a blower type chemical diffusing apparatus as set forth above, characterized in that the chemical retainer has a chemical impregnated body adapted to be heated by heat produced while the fuel cell is generating electric power to volatilize chemical from the chemical impregnated body.

According to the feature of the invention mentioned above, volatilizing chemical by heating the chemical retainer with heat produced during the fuel cell's power generation increases the efficiency of chemical volatilization and allows the chemical retainer to be made small and thereby the apparatus can be used anywhere as desired.

The present invention also provides a blower type chemical diffusing apparatus as set forth above, characterized in that the apparatus body has an air flow passage through which air to flow while the air blower is being driven and that the fuel cell is placed in the said air flow passage.

According to the feature of the invention mentioned above, placing the fuel cell in the air flow passage in the apparatus allows air when the air blower is driven to flow over the fuel cell and product water then produced during its power generation to evaporate. Since this eliminates the need for a water tank or the like, the apparatus can be made less costly and rendered compact.

The present invention also provides a blower type chemical diffusing apparatus as set forth above, characterized in that the fuel cell comprises a cell body and a fuel tank and that the cell body is placed in the air flow passage so that air passes through a space in the cell body in which product water is produced.

According to this feature of the invention, product water produced in a space in the cell body is allowed to evaporate smoothly with air passing through the space.

The present invention also provides a blower type chemical diffusing apparatus as set forth above, characterized in that the apparatus body has an air flow passage through which air to flow while the air blower is being driven, that the fuel cell comprises a cell body and a fuel tank and that the cell body is placed upstream of the chemical retainer in the said air flow passage.

According to this feature of the invention, driving the air blower allows air first to pass through a space in the cell body and then past the chemical retainer into the atmosphere. Since air containing chemical is prevented from flowing through spaces in the cell body, the chemical is prevented from causing any trouble to the cell body. This feature also ensures that the heat produced is utilized concurrently when product water is processed.

The present invention also provides a blower type chemical diffusing apparatus as set forth above, characterized by having a heat emitter, an air blower, a chemical retainer and a fuel cell included in an apparatus body whereby powering the heat emitter to cause it to emit heat with the said fuel cell heats the chemical retainer to cause chemical to volatilize from the chemical retainer and powering the air blower to drive it with the said fuel cell causes such volatilizing chemical to be emitted into an environmental atmosphere.

This feature of the invention promotes the volatilization of chemical into an atmosphere with air flow by the air blower in comparison with the conventional blower type chemical diffusing apparatus, thereby increasing the efficiency of diffusion of volatilizing chemical into an atmosphere.

The present invention also provides a blower type chemical diffusing apparatus as set forth above, characterized by having an ultrasonic generator, an air blower, a chemical retainer and a fuel cell included in an apparatus body whereby powering the ultrasonic generator with the said fuel cell causes ultrasonic waves to be generated therefrom to atomize liquid chemical from the chemical retainer utilizing such ultrasonic waves and powering the air blower to drive it with the said fuel cell causes such atomized chemical to be emitted into an environmental atmosphere.

This feature of the invention increases the efficiency of diffusion of chemical into an atmosphere by promoting, with air flow by the blower, the diffusion of chemical atomized in comparison with the conventional ultrasonic chemical volatilizing apparatus.

The present invention also provides a blower type chemical diffusing apparatus as set forth above, characterized in that the said fuel cell comprises a cell body and a fuel tank and that the said fuel tank is removably included in the apparatus body.

This feature of the invention allows removing the fuel tank from the apparatus body and mounting a new fuel tank as a substitute therefore or refilling the removed fuel tank with fuel, thereby facilitating the replenishment of fuel.

The present invention also provides a blower type chemical diffusing apparatus as set forth above, characterized in that the said fuel cell comprises a cell body and a fuel tank and that the said fuel tank is placed in a peripheral or side section of the apparatus body.

This feature of the invention allows increasing the fuel tank in volume and hence storing a greater amount of fuel in the apparatus body while rendering the entire apparatus thinner.

BRIEF DESCRIPTION OF THE DRAWINGS

These and other objects, features and advantages of the present invention as well as other manners of its implementation will become more readily apparent, and the invention itself will also be better understood, from the following detailed description when taken with reference to the drawings attached hereto showing certain illustrative forms of implementation of the present invention. In the drawings.

BEST MODES FOR CARRYING OUT THE INVENTION

Mention is now made of a first form of implementation of the present invention.

Figure 1:
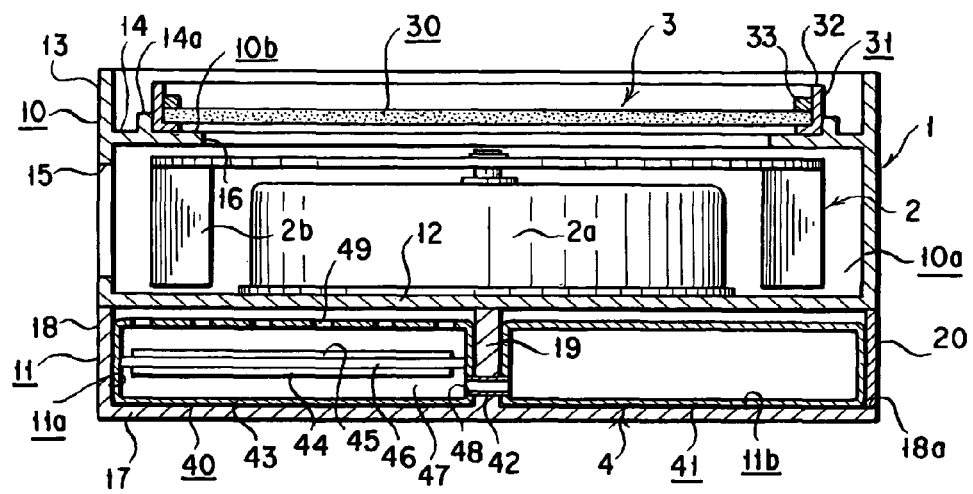
FIG. 1 is a cross sectional view of a blower type chemical diffusing apparatus illustrating a first form of implementation of the present invention.
Figure 2:
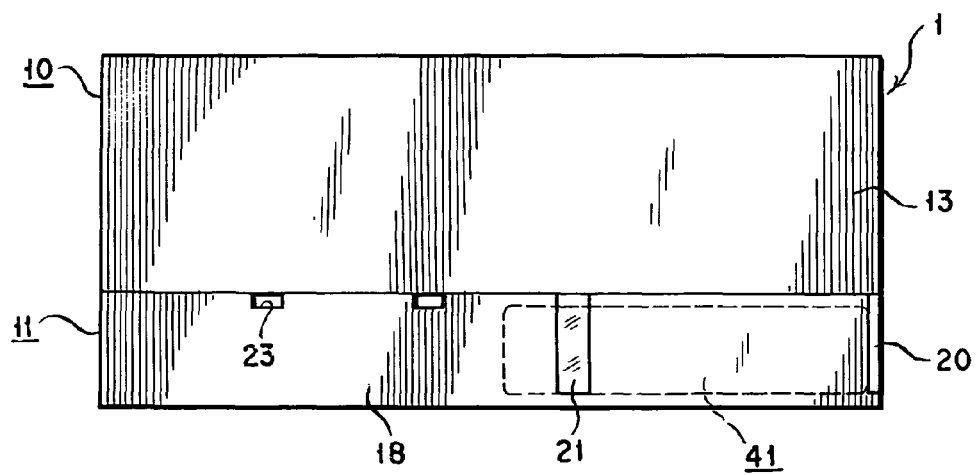
FIG. 2 is a front view of the apparatus shown in FIG. 1.

As shown in FIGS. 1 and 2, a blower type chemical diffusing apparatus of this form of implementation comprises an apparatus body 1 and an air blower 2, a chemical retainer 3 and a fuel cell 4 which are included in the apparatus body 1. The apparatus operates with the air blower 1 driven to generate a wind, which is passed through the chemical retainer 3 to emit chemical therein into an atmosphere.

The apparatus body 1 comprises a main frame 10 and a fuel cell mounting frame 11. The main frame 10 has the air blower 2 and the chemical retainer 3 mounted therein while the fuel cell mounting frame 11 has the fuel cell 4 accommodated therein.

The fuel cell mounting frame 11 is detachably mounted to the main frame 10.

Separating the apparatus body 1 into the main frame 10 and the fuel cell mounting frame 11 in this way allows separating an operation in which the apparatus body 1 is loaded with the air blower 2 and the chemical retainer 3 in the section 10 and an operation in which it is loaded with the fuel cell 4 in the section 11. Thus, the efficiency of loading is increased.

The main frame 10 is shaped in the form of a box, formed of a bottom plate 12, a peripheral plate 13 and a top plate 14. The peripheral plate 13 is formed with an air outlet port 15, the top plate 14 is formed with an air inlet port 16, and the main frame 10 has an air flow chamber 10a formed therein.

Around the air inlet port 16 the top plate 14 has a raised portion 14a forming a shoulder where the upper side of the top plate 14 serves as a chemical carrier mounting section 10b.

Figure 3:
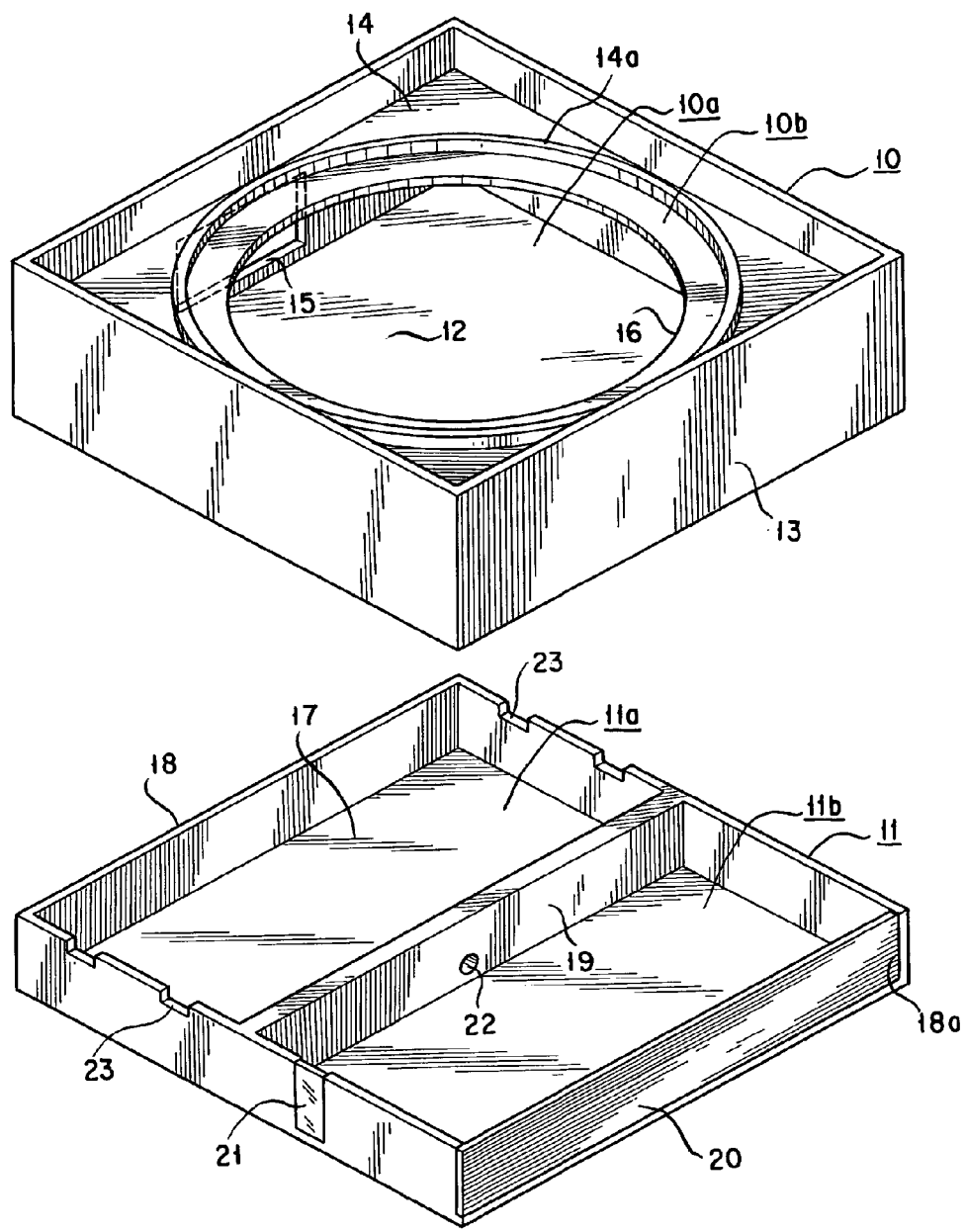
FIG. 3 is a exploded perspective view of an apparatus body and a fuel cell mounting member of the apparatus shown in FIGS. 1 and 2.

The fuel cell mounting frame 11 as shown in FIG. 3 is shaped in the form of a top open box, formed of a bottom plate 17 and a peripheral plate 18 and has its inside divided by a partition plate 19 into a cell body accommodating section 11a and a fuel tank accommodating section 11b.

The peripheral plate 18 where it defines the fuel tank accommodating section 11b has one side formed with a cutout 18a which is opened and closed with a door 20.

The peripheral plate 18 where it defines the fuel accommodating section 11b has another side formed with a see-through section 21, e. g., made of a transparent plate, through which to enable its inside to be visually seen.

The partition plate 19 is formed with a through-hole 22 through which the cell body accommodating section 11a and the fuel tank accommodating section 11b are held in communication with each other.

The peripheral plate 18 that defines the cell body accommodating section 11a has two sides formed with recesses 23 made, for example, from their upper edges.

The air blower 2 has a fan 2b rotated by a motor 2a, which is driven by being powered by the fuel cell 4.

With the fan 2b rotated, air is drawn through the air inlet port 16 into the air flow chamber 10a and discharged through the air outlet port 15.

The chemical retainer 3 comprises a chemical impregnated body 30 in the form of an air-permeable sheet impregnated with chemical and a holder receptacle 31 that carries the chemical impregnated body 30.

The holder receptacle 31 has a receptacle body 32 and a presser ring 33. The chemical impregnated body 30 is placed on the receptacle body 32 and then the presser ring 33 is fitted into the receptacle body 32 to press the chemical impregnated body 30 against the receptacle body 32, thereby holding the chemical impregnated body 30 in position.

Then, the receptacle body 32 is fitted into the inner peripheral section of the raised portion 14a or the retainer mounting section 10b where the chemical retainer 3 is held in place with the chemical impregnated body 30 opposed to the air inlet port 16.

The fuel cell 4 is here a proton-exchange membrane fuel cell, comprising a cell body 40 and a fuel tank 41, which are received in the cell body and fuel tank accommodating sections 11a and 11b, respectively. Fuel in the fuel tank 41 is a liquid fuel containing such as methanol.

For example, the cutout 18a is opened with the door 20 to allow the fuel tank 41 to be inserted and removed as desired. A fuel supply pipe 42 of the fuel tank 41 is passed through the through-hole 22 in the partition plate 19 and connected to a fuel supply port 48 of the cell body 40.

The fuel tank 41 is so made that an amount of fuel in its inside can be visually seen, e. g., a portion of the fuel tank 41 that is opposed to the see-through section 21 is made transparent so that a residual amount of fuel in the fuel tank 41 can be known if the see-through section 21 is visually observed.

Thus, since a residual amount of fuel in the fuel tank 41 can be visually checked through the see-through section 21, correlating such a residual amount of fuel to an effective serviceable time period of the blower type chemical diffusing apparatus allows visually ascertaining not only its operating end point but also the state of its use at any time and hence replenishing or replacing consumables therein such as chemical or chemical retainer at an appropriate time.

Further, visual checkability of a residual amount of fuel prevents its misperception and, with no time aging in connection therewith, gives precise information of an effective operating time period of the apparatus.

To wit, while use was made in the prior art of a color changing pigment for the chemical retainer 3 (chemical impregnated body) in an attempt to visually determine if the end of its effective serviceable time period was being reached through a change in color, the problem arose that a deterioration of a material such as chemical with time tended to be making such a change less clear and harder to see visually.

Mention is made of manners in which to effect this visual checking. Thus, the timing at which the chemical retainer 3 is to be exchanged, such as when the amount of chemical in the chemical retainer 3 has been depleted or when it is so reduced that its efficacy becomes less than satisfactory, is displayed marked with a word such as "End" or "Replace" or a sign or symbol as an indication of that timing at a position on the see-through section at which a preselected amount of fuel is to be seen to remain in the fuel tank so that an arrival at the position can be visually checked.

An indicator to be displayed can be confirmed by actual measurements for a relationship between an amount of fuel that remains in the fuel tank 41 and an amount and/or activeness of chemical that remains in the chemical retainer 3.

To enable checking, the fuel tank 41 may itself be or may have a formed body of a transparent or semi-transparent material and may have a surface provided with an endpoint and/or interim point indication.

To enable checking otherwise, a portion of the apparatus body 1 in which the fuel tank 41 is accommodated may be provided with an open or transparent window as the see-through section 21, the accommodating portion may itself be a formed body of a transparent or semi-transparent material, the accommodating section may be left open, or the door 20 may be provided with an open or transparent window or may be an openable door, and may have a surface provided with an endpoint and/or interim point indication.

Further, the time of exchanging the chemical retainer 3 may be made coincident with the time at which an initial amount of fuel in the fuel tank 41 becomes depleted. In this case, an effective time period of service of the apparatus is established by changing the size of the fuel tank 41 and the maximum amount of fuel accommodated therein.

For example, the fuel tank may be of throwaway type and in this case, upon visually confirming that it has become depleted a new fuel tank and a new chemical retainer are concurrently replaced with. Alternatively, the fuel tank may be of replenishment type in which case, upon visually confirming that it has become depleted, the fuel tank is replenished and concurrently the chemical retainer is replaced with a new chemical retainer. In this case, if the chemical retainer is of replenishment type, it can then be concurrently replenished upon visually confirming that the fuel tank has been depleted.

The cell body 40 is formed of a negative electrode (fuel electrode) 44 and a positive electrode (air electrode) 45 which are opposed to each other across an electrolyte layer 46 in a receptacle 43.

The negative electrode 44 acts to oxidize fuel, thereby taking out electrons and protons from fuel and has a structure in which catalyst and gas permeable layers are laid one on another. The negative electrode 44 has one of its ends provided with a negative terminal (not shown).

The positive electrode 45 is designed to produce water by causing protons arriving from the negative electrode 44 to react with oxygen ions generated when oxygen is reduced by electrons arriving from the negative electrode 44 via an external circuit. For example, it has a structure like that of the negative electrode 44.

The positive electrode 45 has one of its ends provided with a positive terminal (not shown).

The electrolyte layer 46 is designed to transport protons generated at the negative electrode 44 to the positive electrode 45, and is composed of a material that is not electronically conductive but capable of transporting protons.

In the reaction process mentioned above, a potential difference is produced between the negative and positive electrodes 44 and 45, thereby generating electric power.

At its one side opposite to the electrolyte layer 46, the negative electrode 44 is provided adjacent thereto with a fuel retaining space 47, which has the abovementioned fuel supply port 48 formed to communicate with a fuel supply port of the adjacent fuel tank 41 via the fuel supply pipe 42. Thus, to supply the negative electrode 44 with fuel, the fuel retaining space 47 is held in communication with the inside of the fuel tank 41 via the fuel supply port 48 and the fuel supply pipe 42 so that the fuel retaining space 47 is filled with fuel from the fuel tank 41.

On the other hand, the positive electrode 45 at its one side opposite to the electrolyte layer 46 is provided with an air permeable or ventilated structure apertured to allow the positive electrode 45 to be supplied naturally with environmental air, e. g., with vent holes 49 formed in the receptacle 43. Further, water produced as mentioned above is allowed to escape by natural vaporization and expelled into the atmosphere via such apertures.

As to the arrangement of the cell body 40 and the fuel tank 41 in the fuel cell 4, while the cell body 40 and the fuel tank 41 are shown disposed side by side and coupled together horizontally in this form of implementation, they may be placed one on the other and coupled together vertically. In this case, for example, the accommodating section may be formed at its bottom with an openable door to allow taking the fuel tank 41 into and out of the accommodating section. Further, they may be spaced apart and coupled together.

The fuel cell mounting frame 11 may be an integral part of the main frame 10.

Mention is next made of a second form of implementation of the present invention.

This form of implementation is identical in makeup to the first form except that the cell body 40 is positioned below the air blower 2 (in the main frame 10 of the apparatus body 1) and the fuel tank 41 laterally of the air blower 2 (in the main frame 10 of the apparatus body 1).

Figure 4:
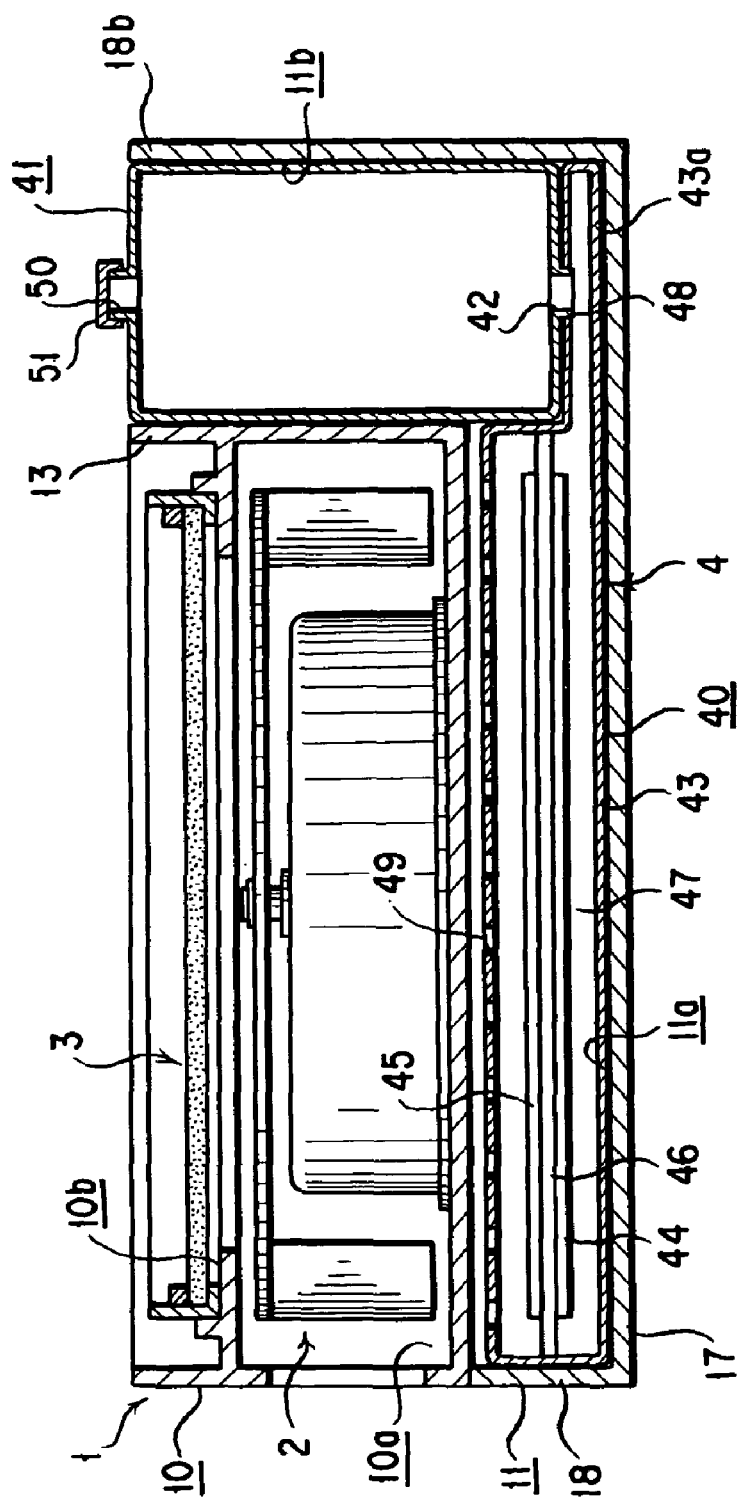
FIG. 4 is a cross sectional view of a blower type chemical diffusing apparatus illustrating a second form of implementation of the present invention.

Specifically, the peripheral plate 18 of the fuel cell mounting frame 11 as shown in FIG. 4 has a portion at one side lower and a portion at the other side higher, this higher peripheral portion 18b that is U-shaped in planar configuration forming a fuel tank accommodating section 11b together with a portion of the peripheral plate 13 of the main frame 10.

Figure 5:
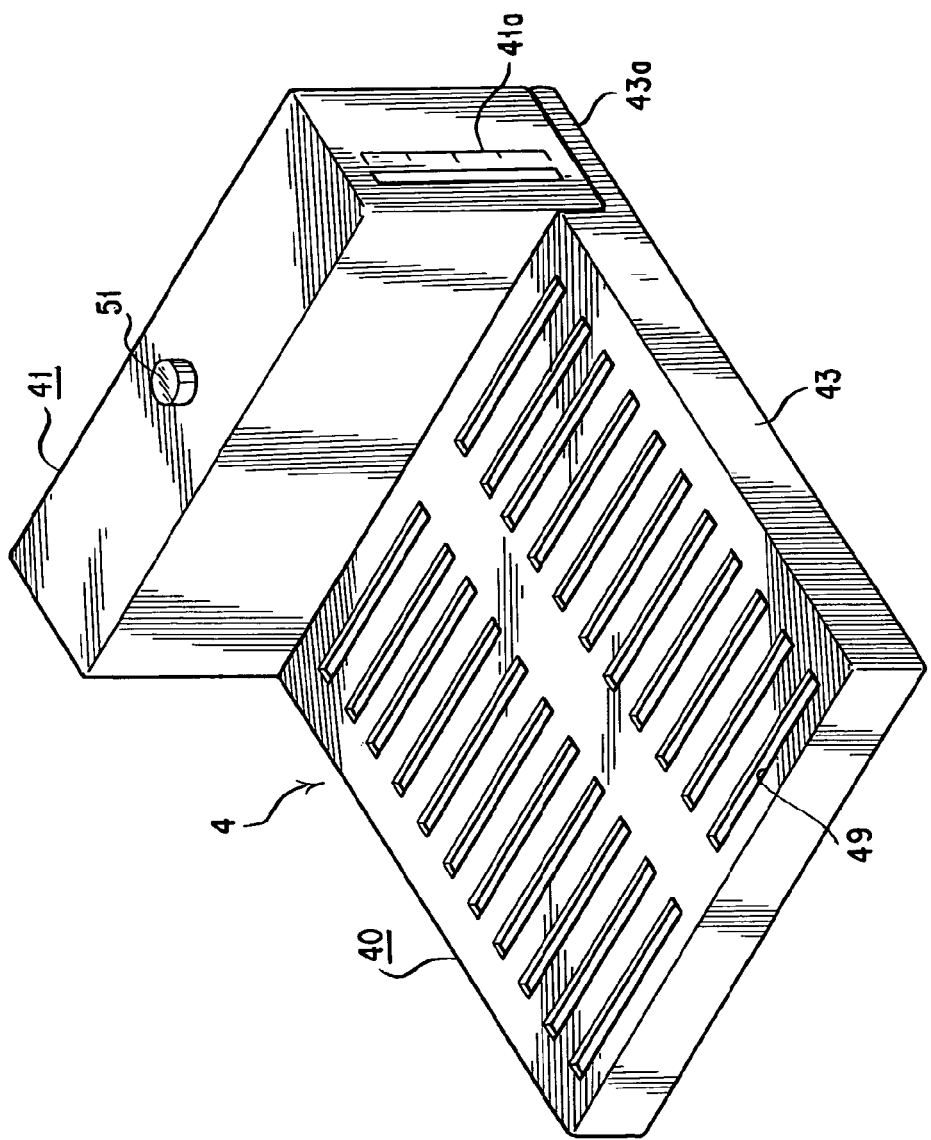
FIG. 5 is a perspective view of a fuel cell in the apparatus shown in FIG. 4.

As shown also in FIG. 5, the receptacle 43 of the cell body 40 has an extension 43a which extends into the fuel tank accommodating section 11b and on which the fuel tank 41 is placed in contact therewith. Shown by reference number 41a in FIG. 5 is a residual quantity display for the fuel tank 41.

The extension 43a of the receptacle 43 is formed in its upper face with the fuel supply port 48 which communicates with the fuel retention space 47.

The fuel tank 41 is formed through its bottom face with the fuel supply pipe 42 which is sized and positioned so that it fits with the fuel supply port 48 when the fuel tank 41 is fitted in the fuel tank accommodating section 11b.

The fuel tank 41 is provided with a feed opening 50 through which to feed fuel and which is opened and closed when a cap 51 is fitted and removed.

In this form of implementation, too, the fuel cell mounting frame 11 may be an integral part of the main frame 10.

This can be done by structuring the apparatus body 1 continuously so that it has the cell body mounting section 11a lying below the airflow chamber 10a, the top open fuel tank accommodating section 11b lying laterally of the airflow chamber 10a, and the cell body accommodating section 11a having an end extension extending to an extent below the fuel tank accommodating section 11b.

Mention is next made of a third form of implementation of the present invention.

This form of implementation is identical in makeup to the first form except that the fuel cell 4 is disposed laterally of the air blower 2.

Figure 6:
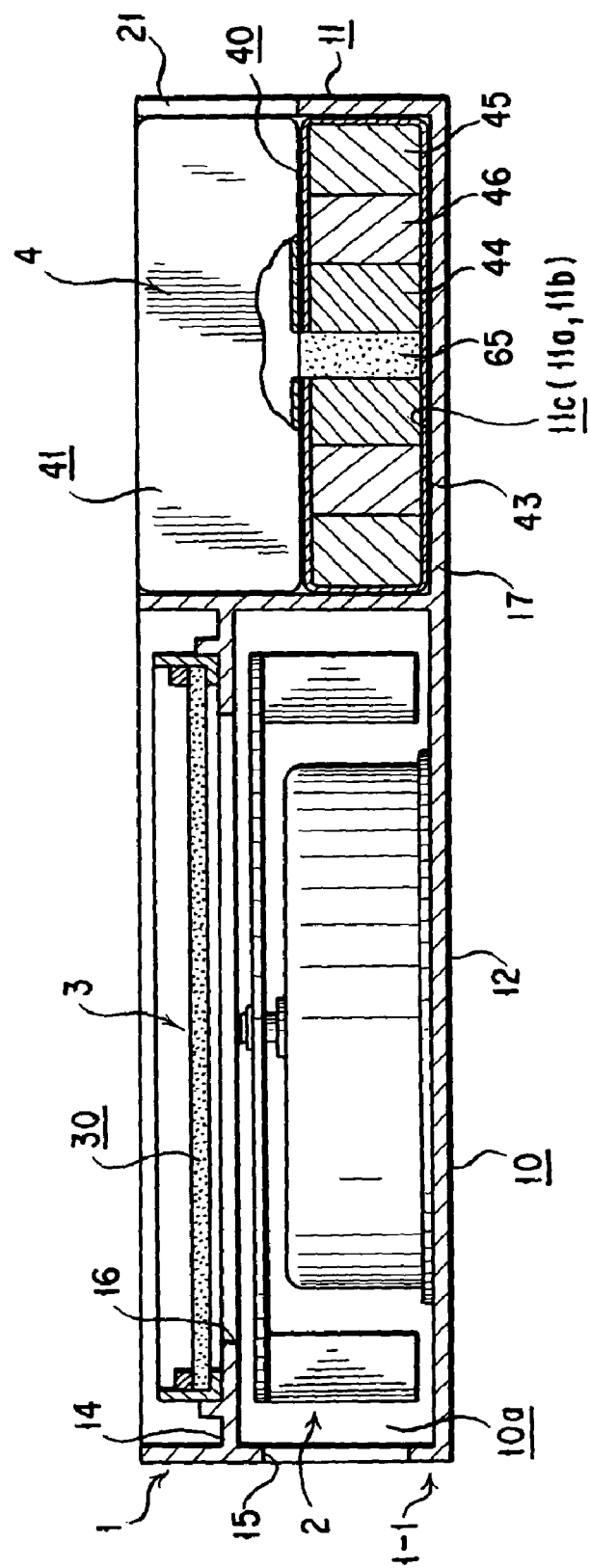
FIG. 6 is a cross sectional view of a blower type chemical diffusing apparatus illustrating a third form of implementation of the present invention.

Specifically, the apparatus body 1 as shown in FIG. 6 has the main frame 10 and the fuel cell mounting frame 11 whose respective bottom plates 12 and 17 are made integral and continuous with each other so as to form the airflow chamber 10a and a top open recess 11c adjoining each other.

Figure 7:
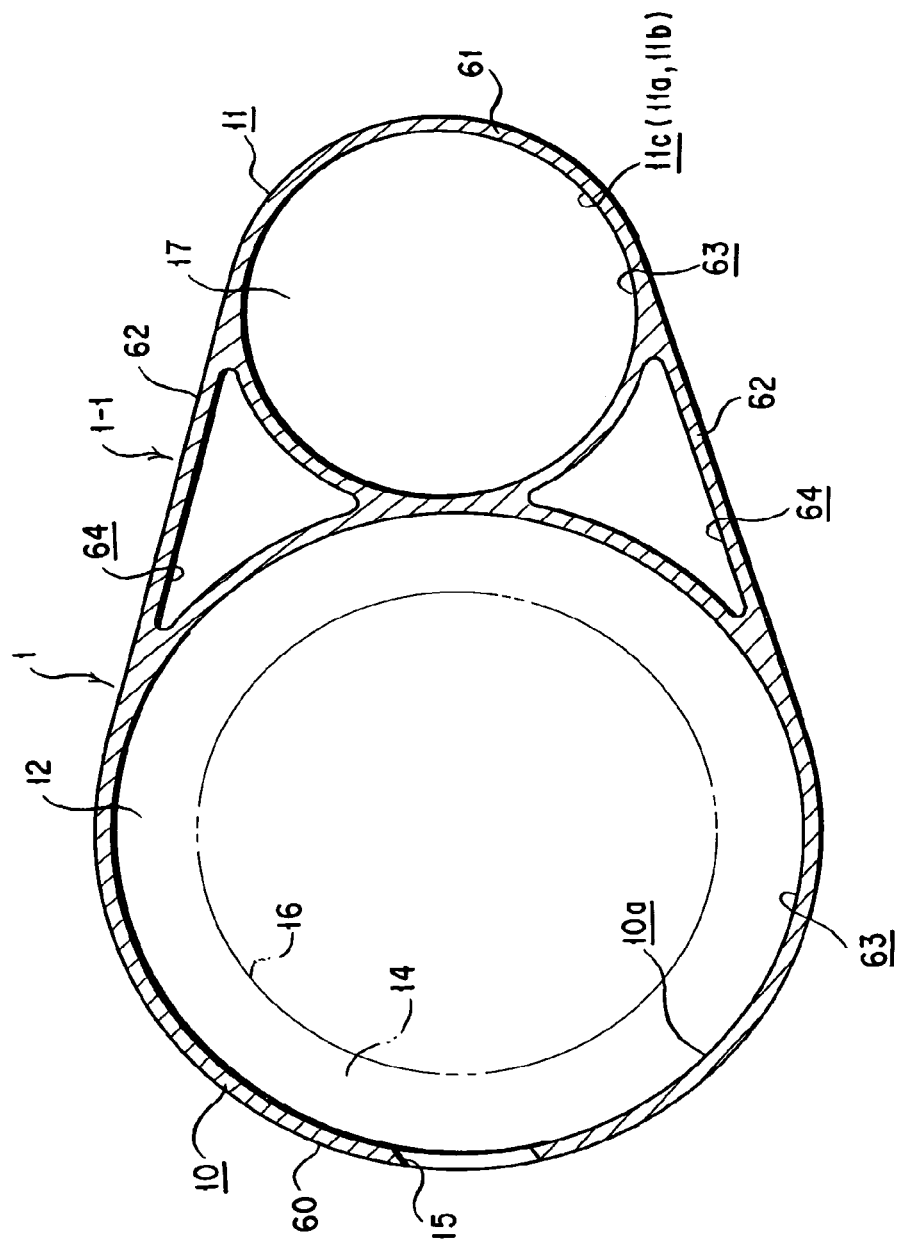
FIG. 7 is a transverse sectional view of an apparatus body of the apparatus in shown in FIG. 6.

For example, as shown in FIG. 7 the main frame 10 to form the apparatus body 1 comprises a first cylindrical plate 60, a second cylindrical plate 61 and two vertical plates 62 connecting the first and second cylindrical plates 60 and 61 continuously together to form a peripheral plate 1-1 while defining a first and a second cylindrical section 63 and two generally triangular (hollow prism) sections 64, which are closed at their lower ends with the bottom plates 12 and 17 of the apparatus body 1 mentioned above. The top open recess 11c mentioned above is thus defined with the second cylindrical section 63 formed of the second cylindrical plate 61.

And, the first cylindrical plate 60 is formed with an inner annular plate forming the abovementioned top plate 14 to define the airflow chamber 10a.

The second cylindrical plate 61 in which the fuel tank 41 is to lie opposed thereto is in part cut out to provide the see-through section 21.

Since in this form of implementation the top open recess 11c (namely, providing both the cell body and fuel tank accommodating sections 11a and 11b) is circular in section, the fuel cell 4 is of a cylindrical body in shape in which lie, from inner to outer, the negative electrode 44, the electrolyte layer 46 and the positive electrode 45 in contact with one another and at its center a rod shaped fuel supply element 65 that communicates with the fuel tank 41.

As to the manner in which to mount the fuel cell 4, while the cell body 40 is shown fastened to the apparatus body 1 with the fuel tank 41 made detachable, the cell body 40 and the fuel tank 41 may be made integral and detachable together for their exchange jointly. In this case, the fuel tank 41 may be provided with the fuel feed opening 50 and the cap 51 for the replenishment of fuel.

Also, the fuel cell so integrated may be provided as a discrete body physically separate from but connectable to the apparatus body 1 via connecting means provided for them, respectively, for use of the apparatus.

Mention is next made of a fourth form of implementation of the present invention.

This form of implementation is identical in makeup to the previous forms of implementation except that the chemical retainer 3 and the fuel tank 41 are so made that they can together and concurrently be mounted and dismounted.

Figure 8:
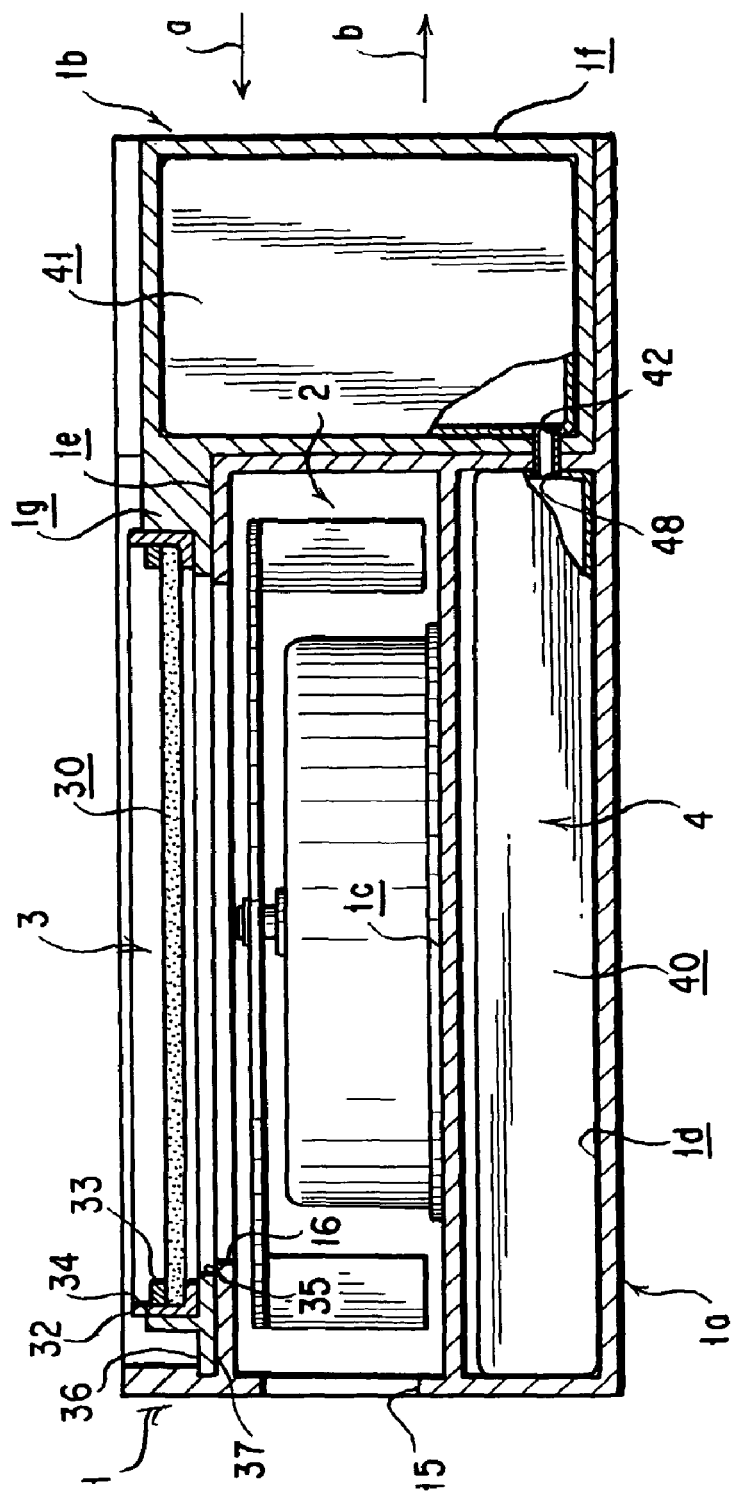
FIG. 8 is a cross sectional view of a blower type chemical diffusing apparatus illustrating a fourth form of implementation of the present invention.
Figure 9:
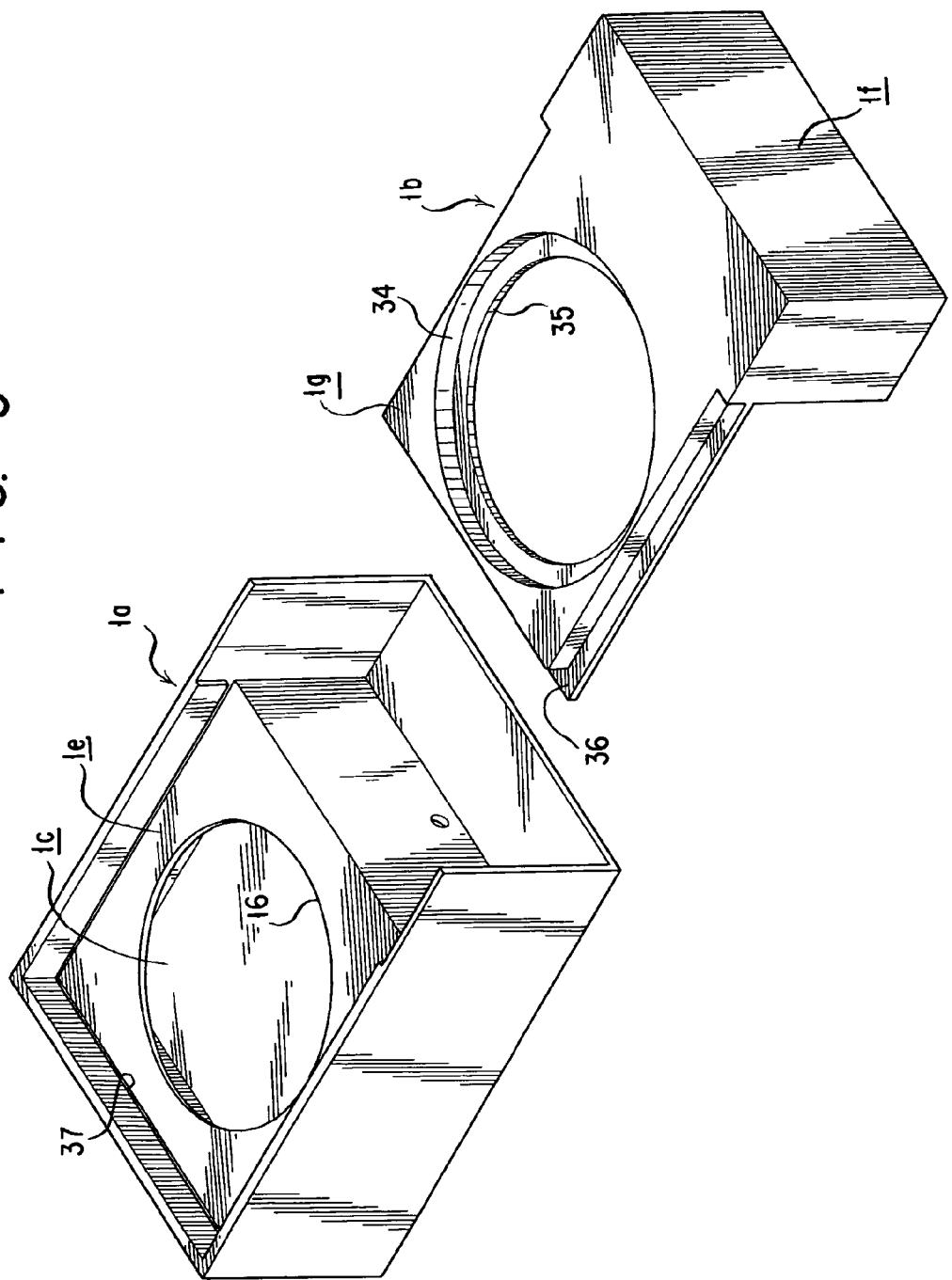
FIG. 9 is a exploded perspective view of an apparatus body and a movable part of the apparatus shown in FIG. 8.

Specifically, as shown in FIGS. 8 and 9 the apparatus body 1 comprises a fixed part 1a and a movable part 1b which are constructed and arranged so as to enable the movable part 1b to be attached to and detached from the fixed part 1a by sliding the movable part 1b into and away from the fixed part 1a in the directions of arrows a and b indicated, respectively.

The fixed part 1a has the air blower 2 and the cell body 40 secured thereto and the movable part 1b has the chemical retainer 3 and the fuel tank 41 mounted thereto.

Enabling the chemical retainer 3 and the fuel tank 41 to be dismounted together and concurrently in this manner allows replenishing or replacing chemical and fuel concurrently without entailing their ineffective consumption, if respective amounts of chemical in the chemical retainer 3 and of fuel in the fuel tank 41 are adjusted so that the fuel tank 41 becomes depleted of fuel when the chemical retainer 3 is depleted of chemical by diffusion into the atmosphere.

The fixed part 1a is generally in the form of a box having top and one side open and is formed with an airflow chamber 1c between top and bottom in an area closer to the other side, a cell body accommodating section 1d below the air flow chamber 1c and has a movable part accommodating section 1e formed by a space above the airflow chamber 1c in the area and a space between top and bottom at the one side.

The airflow chamber 1c is formed at its top with the air inlet port 16 and laterally with the air outlet port 15.

The airflow chamber 1c has the air blower 2 mounted therein and the cell body accommodating section 1d has the cell body 40 mounted therein.

The movable part 1b is generally in the form of character L in section as a whole having a thick, fuel tank mounting frame 1f and a thin, chemical retainer mounting frame 1g, and is adapted to be slide-ft into the movable part accommodating section 1e of the fixed part 1a as it is moved in the direction of arrow a and to be detached as it is moved in the direction of arrow b.

The chemical retainer mounting frame 1g is formed with a stepped hole comprising a large and a small hole 34 and 35, and the large hole 34 has a diameter such as to allow the chemical retainer 3 to be fitted therein and seated on a shoulder of the stepped hole and thereby mounted on the frame 1g.

The movable part 1b and the fixed 1a are so configured that when the former as it is moved in the direction of arrow a is slit into the latter to take the position shown in FIG. 8, the fuel supply pipe 42 of the fuel tank 41 is fitted into the fuel supply port 48 of the cell body 40.

At the same time, a protruding strip 36 formed on the chemical retainer mounting frame 1g is allowed to engage with an engagement recess 37 formed in the fixed part 1a whereby the two parts 1a and 1b are fastened together.

When this state is reached, the chemical impregnated body 30 received in the chemical retainer 3 comes to face the air inlet port 16.

Sliding the movable part 1b from the position shown in FIG. 8 towards the direction of arrow b will extract the fuel supply pipe 42 from the fuel supply port 48 and at the same time the protruding strip 36 from the engagement recess 37, whereby the movable part 1b is removed from the fixed part 1a.

Mention is next made of a fifth form of implementation of the present invention.

This form of implementation is identical in makeup to the first form except that the fuel tank 41 is disposed to lie around the apparatus body 1.

Figure 10:
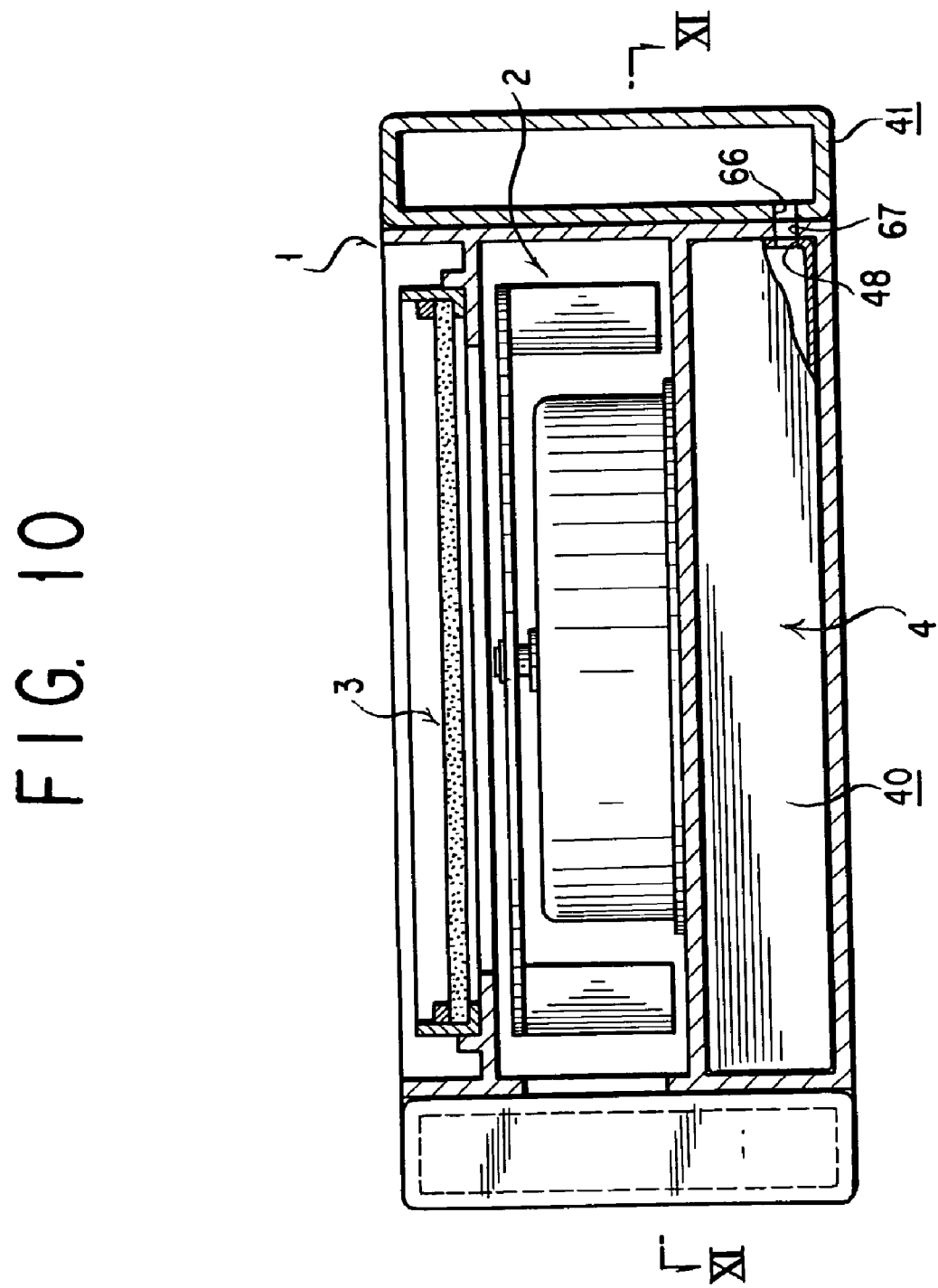
FIG. 10 is a cross sectional view of a blower type chemical diffusing apparatus illustrating a fifth form of implementation of the present invention.

Specifically, as shown in FIG. 10 the chemical retainer 3 is mounted on top of the apparatus body 1, the air blower 2 is mounted in a space between its top and bottom and the cell body 40 is mounted below the air blower 2 on the bottom.

The fuel tank 41 is generally in the form of a ring such that it can be detachably fitted on the peripheral surface of the apparatus body 1 and thereby mounted thereon.

The apparatus body 1 is formed with a hole 67 through which a fuel outlet port 66 of the fuel tank 41 is to communicate with the fuel supply port 48 of the cell body 40.

Since this allows increasing the capacity of the fuel tank 41, an apparatus can be provided capable of storing an increased amount of fuel and hence capable of power generation for an extended period of time.

Also, since the apparatus body is reduced in height or vertical size, a blower type chemical diffusing apparatus can be provided that is smaller in thickness.

In the form of implementation shown in FIG. 10 wherein the fuel tank 41 is identical in height or vertical size to the apparatus body 1 and disposed around the chemical retainer 3, the air blower 2 and the cell body 40, its capacity can be augmented.

Figure 11:
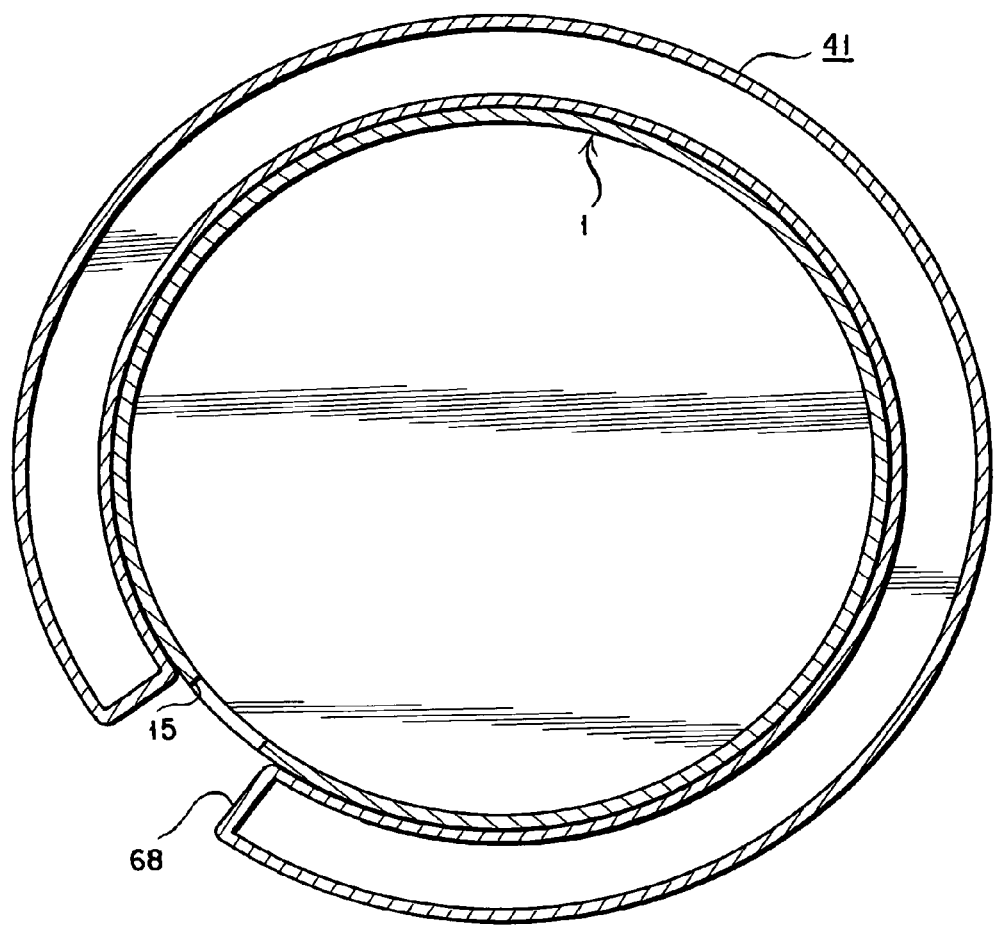
FIG. 11 is a cross sectional view taken along the line XI-XI in FIG. 10 with the air blower omitted.

Further, being generally ring-shaped disposed so as to surround the air blower 2, the fuel tank 41 is here so designed that it does not block the air outlet port 15 of the apparatus body 1. For example, as shown in FIG. 11 the fuel tank 41 may be in the form of a discontinuous ring with an opening 68 that faces the air outlet port 15 of the apparatus body 1 so that air flowing out through the air outlet port 15 can be emitted through the opening 68 into the atmosphere.

Although not shown, the fuel tank 41 may be positioned so as to only surround the cell body 40, or the fuel tank 41 may be disposed to surround the cell body accommodating frame that is made smaller than the air blower 2 of the apparatus body 1.

In these cases as well, the air outlet port 15 is prevented from facing the fuel tank 41 which is still generally ring-shaped.

Also, the apparatus body 1 may, although not shown, have a pair of concentric peripheral plates between which a top open, generally ring-shaped recess may be formed so as to surround both the airflow chamber and the cell body accommodating frame, and in this recess the fuel tank 41 may be fitted and thereby mounted.

Also, although not shown a plurality of fuel tanks 41 may be provided one of which is used to communicate with the cell body 40 and the others of which are used as spares.

While water product of the fuel cell 4 is shown processed as it naturally evaporates, such water product may be allowed to collect in a water tank and stored therein.

For example, in the arrangement shown in FIG. 1 such water tank (not shown) may be disposed adjacent to the cell body 40.

In the arrangement of FIG. 4 such water tank (not shown) may be disposed adjacent and parallel to the fuel tank 41 in the fuel tank accommodating section 11b.

Figure 12:
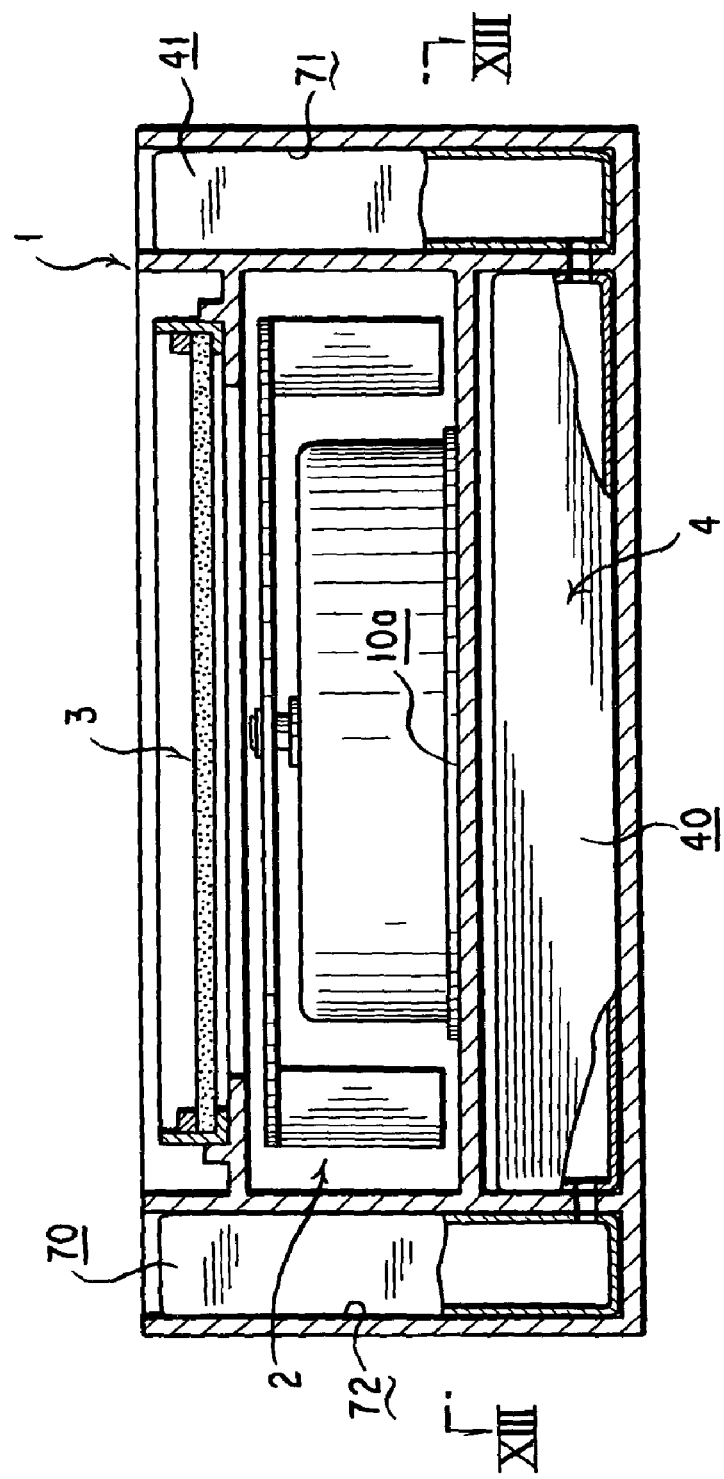
FIG. 12 is a cross sectional view of a blower type chemical diffusing apparatus illustrating a sixth form of implementation of the present invention.

Also, where as in a sixth form of implementation as shown in FIG. 12 the fuel tank 41 is disposed at one side of the apparatus body 1, such water tank 70 may be disposed at its other side.

Figure 13:
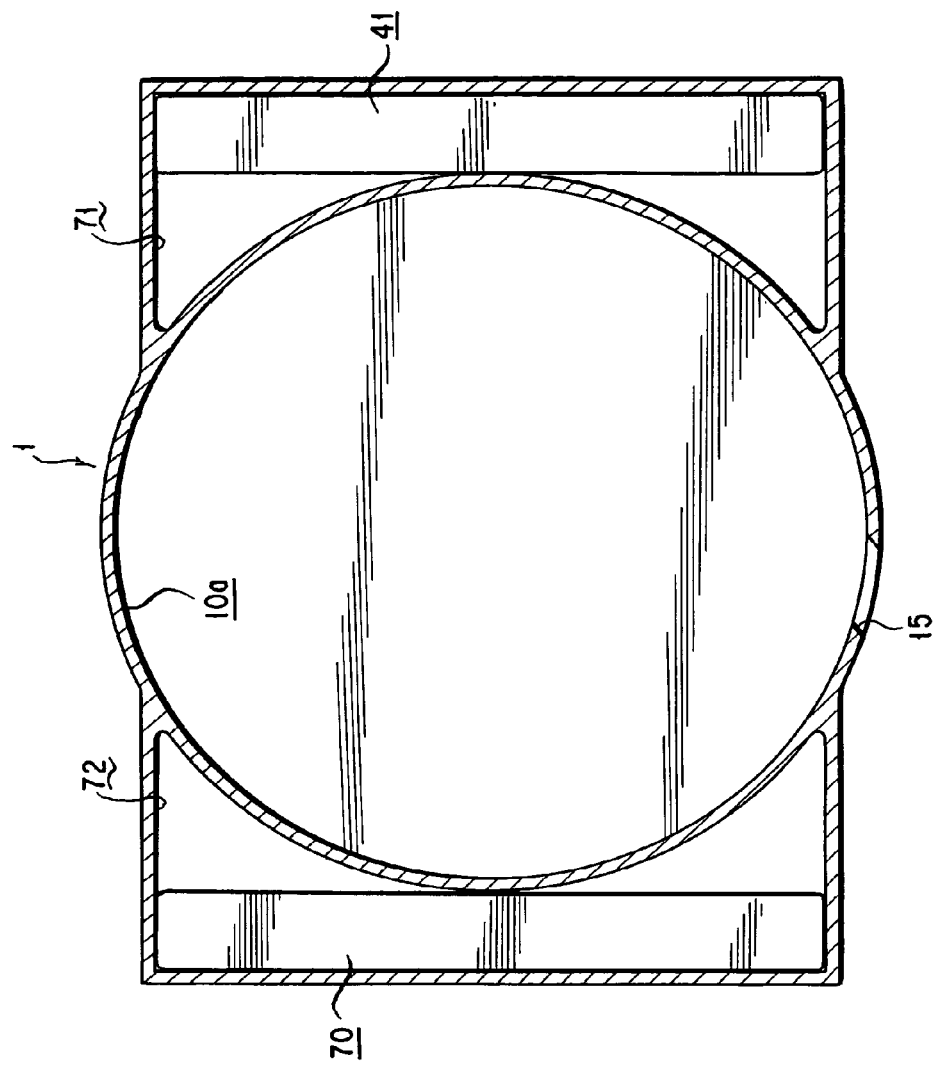
FIG. 13 is a cross sectional view taken along the line XIII-XIII in FIG. 12 with the air blower omitted.

For example, as shown in FIG. 13 the apparatus body 1 may have a first, top open recess 71 formed at its one side and a second, top open recess 72 formed at its other side.

Then, the fuel tank 41 and the water tank 70 may be accepted and thereby mounted in the first and second recesses 71 and 72, respectively.

In this case, the first and second recesses 71 and 72 should, of course, be formed so as to prevent them from blocking the air outlet port 15.

If the water tank is provided in any manner as mentioned above, an amount of water storage there may be made visually checkable to allow using it as a measure of an endpoint (end of use), thereby ascertaining a time of exchange of the chemical retainer 3 and/or the fuel tank 41.

In connection with the first to six forms of implementation of the present invention mentioned above, it should be noted that the apparatus body 1 may be embodied in various forms including making the main frame 10 and the fuel cell mounting frame 11 separately from or integrally with each other, making the fuel cell 4 and/or the fuel tank 41 detachable for reattachment, and making the main frame 10 (including the cell body) and the fuel tank 41 separately from each other. Further, the power magnitude of the fuel cell 4, the rate of airflow in and from the main frame 10, the quantitative scale of chemical for diffusion from the chemical retainer 3 and the form of the apparatus such as if it is of portable or fixed type can be embodied variously, depending on particular purposes and applications of the apparatus.

Also, the fuel cell 4 may be positioned below and/or laterally of the air blower 2 (or the main frame 10 of the apparatus body 1), that is at a position accessible easily and conveniently depending on a particular purpose or application of the apparatus. A particular position at which to position the fuel cell 4 is also selected for the sake of simplicity and economy of manufacture.

Also, in mounting the cell body 40, there are no particular limitations in relative positions of its negative and positive electrodes 44 and 45 and the fuel tank 41 if they are at least such that the negative and positive electrodes 44 and 45 are supplied, respectively, with amounts of fuel and of air which are sufficient not to hinder power generation by the fuel cell 4.

There is also no particular limitation in the shape of the blower type chemical diffusing apparatus of the invention or the apparatus body 1; it may illustratively be circular, square, triangular or polygonal.

There is also no particular limitation in the shape of a component in which the fuel cell is accommodated; illustratively it may be circular, square, triangular or polygonal. And, neither is there in the shape of the fuel tank 41; it may illustratively be circular or square. Also, they may have different shapes which may be combined.

Mention is next made of a seventh form of implementation of the present invention.

Figure 14:
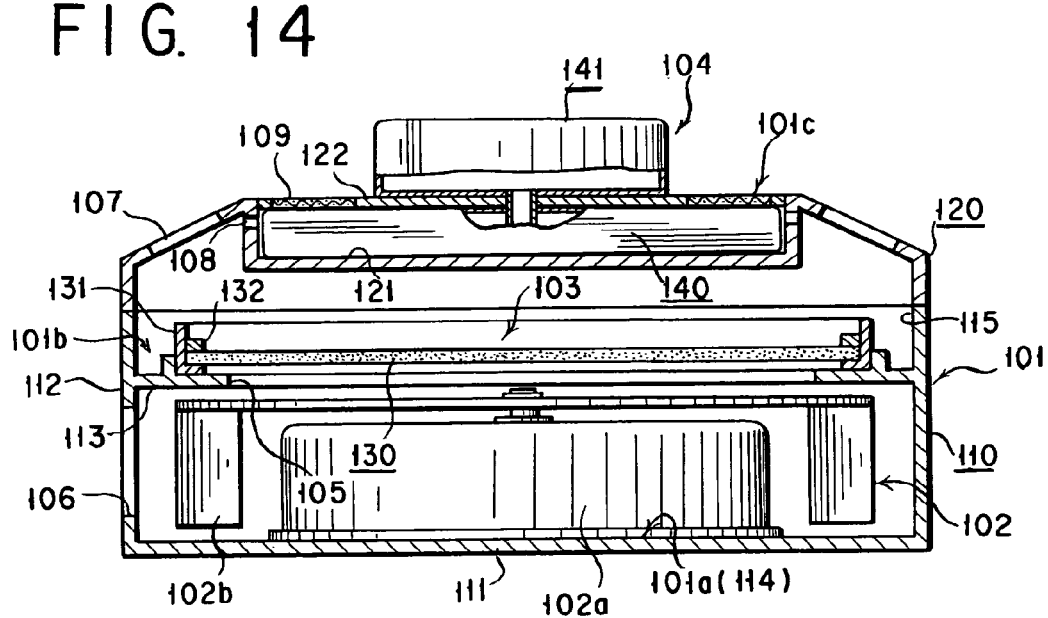
FIG. 14 is a cross sectional view of a blower type chemical diffusing apparatus illustrating a seventh form of implementation of the present invention.
Figure 15:
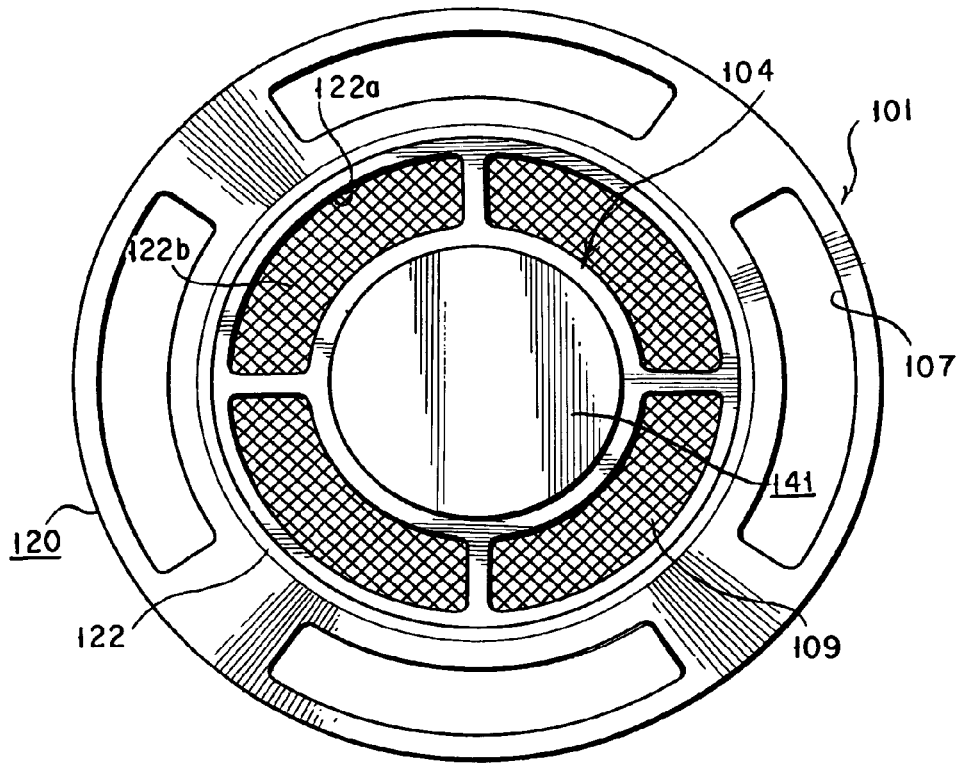
FIG. 15 is a plan view of the apparatus shown in FIG. 14.

As shown in FIGS. 14 and 15, a blower type chemical diffusing apparatus of this form of implementation comprises an apparatus body 101, and an air blower 102, a chemical retainer 103 and a fuel cell 104 which are included in the apparatus body 101.

Driving the air blower 102 producers air flows in air current passages in the apparatus body 101 to cause chemical from the chemical retainer 103 to be entrained in air and to emitted into the atmosphere. In this form of implementation, air is passed to flow through the chemical retainer 103, thereby causing chemical therein to volatilize and the volatilizing chemical to be emitted, as it is entrained in air, into the atmosphere.

The air blower 102 is powered by the fuel cell 104 as its power supply.

The fuel cell 104 is disposed in an air current passage, namely in an airflow passage by the air blower 102 so that air is forced to flow by the air blower 102 over the fuel cell 104 to evaporate water product produced during the power generation by the fuel cell 104.

With the apparatus so constructed, product water produced during the power generation by the fuel cell 104 is processed by vaporization with air flows produced by the air blower 102 used to cause diffusion of chemical.

As a result, the apparatus no longer requires a water tank, becomes less costly and can be reduced in total size.

Also, air flowing in the air current passage in which the fuel cell 104 is disposed is heated by heat generated by the fuel cell, becoming warm air which serves to accelerate the emission of chemical. Also, since a chemical that is so low in vapor pressure that it cannot produce its emission with blast alone can here be emitted, the types of chemicals that can be used are increased.

For example, the apparatus body 101 includes an air flow chamber 101a, a chemical accommodating chamber 101b and a fuel cell mounting section 101c wherein the airflow chamber 101c communicates with the chemical accommodating chamber 101b via an air inlet port 105 and is open to the outside via an air outlet port 106, and the chemical accommodating chamber 101b is open to the outside via main inflow ports 107 and communicates with the outside via outflow ports 108 and inflow ports 109 formed in the fuel cell mounting section 101c.

Thus, driving the air blower 102 causes air to flow through the main inflow ports 107 into the chemical accommodating chamber 101b and at the same time air to flow through the inside of the fuel cell 104 into the chemical accommodating chamber 101b.

Air flowing into the chemical accommodating chamber 101b is allowed to flow past the chemical retainer 103 into the atmosphere through the air outlet port 106.

Air current passages in which air is forced to flow with the air blower 102 driven are thereby formed in the apparatus body 101.

To wit, the main inflow ports 107, the air inlet port 105 and the air outlet port 106 provide a main air current passage while the inflow ports 107 and the outflow ports 108 provide a subsidiary air current passage joining the main air current passage and having the fuel cell 104 disposed therein.

With the apparatus so constructed, the chemical retainer 103 through which air flowing in the main air current passage is passed is not impeded from emitting chemical into the atmosphere.

In this form of implementation, it will also be noted that the chemical retainer 103 is separated from the air blower and that in the air current passages, the fuel cell 104 is disposed upstream of the chemical retainer 103 which in turn lies upstream of the air blower 102.

A specific example is next given of the configurations of these members.

The apparatus body 101 comprises a main frame 110 and a fuel cell mounting frame 120.

The main frame 110 is formed of a bottom plate 111, a peripheral plate 112 and a top plate 113, generally in the form of a box having a hollow 114 and a top open recess 115 wherein the peripheral plate 112 and the top plate 113 are formed with the air outlet port 106 and the air inlet port 105, respectively, the hollow 114 constituting the airflow chamber 101a.

The fuel cell mounting frame 120 is removably mounted on the upper end of the peripheral plate 112 of the main frame 110 while defining the chemical accommodating chamber 101b with the top plate 113.

The fuel cell mounting frame 120 is formed at its center with a top open recess section 121 which is closed with a lid 122, and is also formed closer to the top of the recess section 121 with the outflow ports 108 and in the lid 122 with the inflow ports 109, the recess section 121 and the lid 122 defining the fuel cell mounting section 101c. For example, the lid 122 is formed with a plurality of openings 122a provided with nets 122b to form the inflow ports 109.

The air blower 102 comprises a motor 102a and a fan 102b wherein the motor 102a is powered by the fuel cell 104 as its power supply.

The chemical retainer 103 comprises a chemical impregnated body 130 in the form of an air permeable sheet impregnated with chemical, a retainer receptacle 131 in which the chemical impregnated body 130 is fitted, and a hold ring 132 that is fitted and thereby mounted in the retainer receptacle 131.

The chemical retainer 103 is mounted so that its retainer 131 is fitted in the top plate 113 and then the chemical impregnated body 130 faces the air inlet port 105. Thus, the chemical retainer 103 is separated from the air blower 102 (with the fan 102b).

The fuel cell 104 is made up of a cell body 140 and a fuel tank 141.

The cell body 140 is received in the recess section 121 and the fuel tank 141 is removably mounted on the lid 122.

Figure 16:
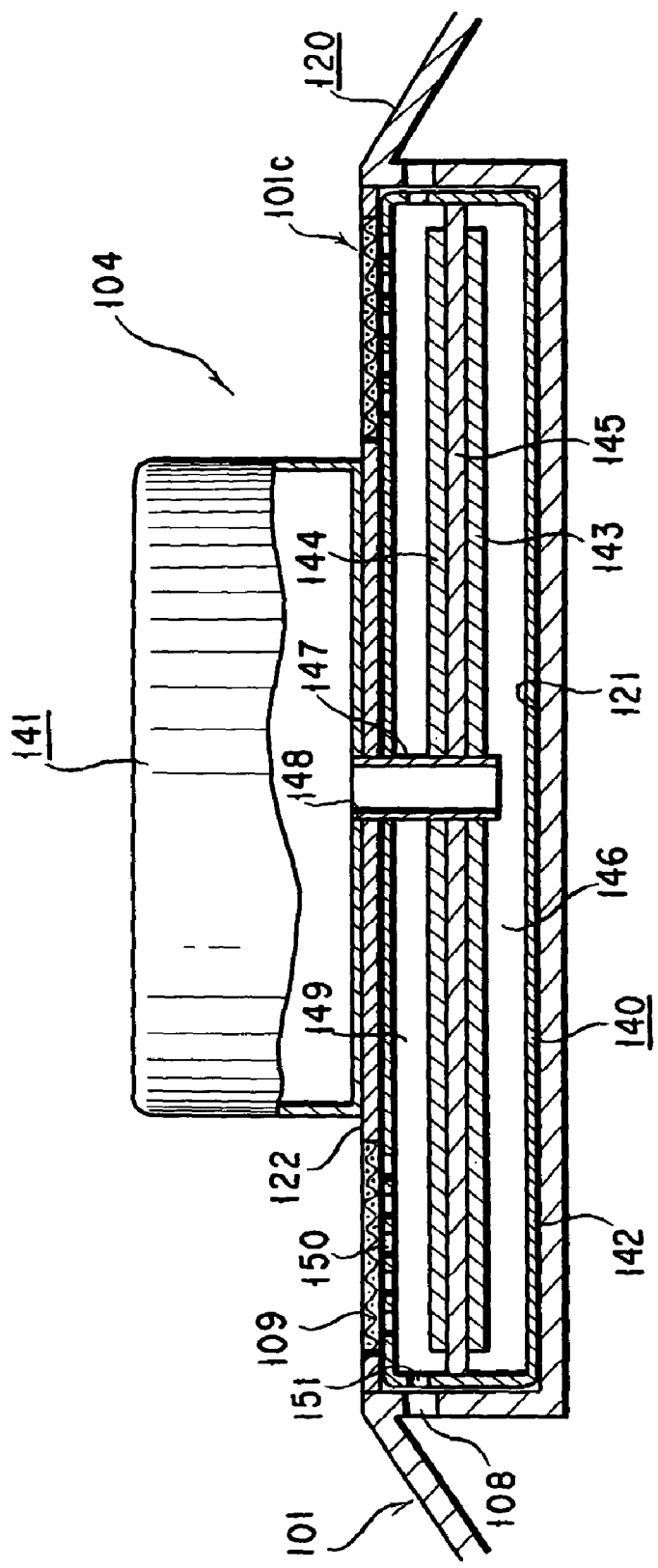
FIG. 16 is an enlarged cross sectional view of a fuel cell mounting part in the apparatus shown in FIGS. 14 and 15.

The cell body 140 as shown in FIG. 16 is in the form of a flat plate accommodated in a cell receptacle 142 and has a negative (fuel) electrode 143 and a positive (air) electrode 144 which are opposite to each other across an electrolyte layer 145. The negative electrode 143 is adapted to oxidize fuel and take electrons and protons from fuel and has a structure in which a catalyst layer and a gas layer are laminated. The negative electrode 143 has its end provided with a negative terminal (not shown).

The positive electrode 144 is designed to produce water by causing protons arriving from the negative electrode 143 to react with oxygen ions generated when oxygen is reduced by electrons arriving from the negative electrode 143 via an external circuit. For example, it has a structure like that of the negative electrode 143. The positive electrode 144 has its end provided with a positive terminal (not shown).

The electrolyte layer 145 is designed to transport protons generated at the negative electrode 143 to the positive electrode 144, and is composed of a material that is not electronically conductive but capable of transporting protons.

In the reaction process mentioned above, a potential difference is produced between the negative and positive electrodes 143 and 144, thereby generating electric power.

At its one side opposite to the electrolyte layer 145, the negative electrode 143 is provided adjacent thereto with a fuel retaining space 146, which is supplied with fuel in the fuel tank 141 through a fuel supply pipe 147.

The fuel supply pipe 147 is attached to the lid 122 upon passing upwards through the negative electrode 143, the electrolyte layer 145, the positive electrode 144 and the lid 122, and has its projecting end fitted with a supply port 148 of the fuel tank 141.

Fuel in the fuel tank 141 is a liquid fuel including methanol. Also, the fuel tank 141 is removably mounted so that upon depleting fuel it can be detached from the lid 122 for reloading with fuel and reattachment or for replacement with a new fuel tank.

The positive electrode 144 at its one side opposite to the electrolyte layer 145 is provided with a space 149 in contact thereto in which product water is produced.

This space 149 communicates with the inflow ports 109 and the outflow ports 108. For example, it communicates with the inflow ports 109 and the outflow ports 108 via inlet ports 150 and outlet ports 151, respectively, which are formed in the cell receptacle 142.

With the apparatus so constructed, air is forced by the air blower 102 to flow in the space 149 where product water can be vaporized.

While in this form of implementation, the fuel supply pipe 147 is shown to pass through the negative electrode 143, the electrolyte layer 145 and the positive electrode 144, the fuel supply pipe 147 may be positioned laterally of the receptacle 142 to penetrate through the receptacle 142 into the fuel retention space 146.

Figure 17:
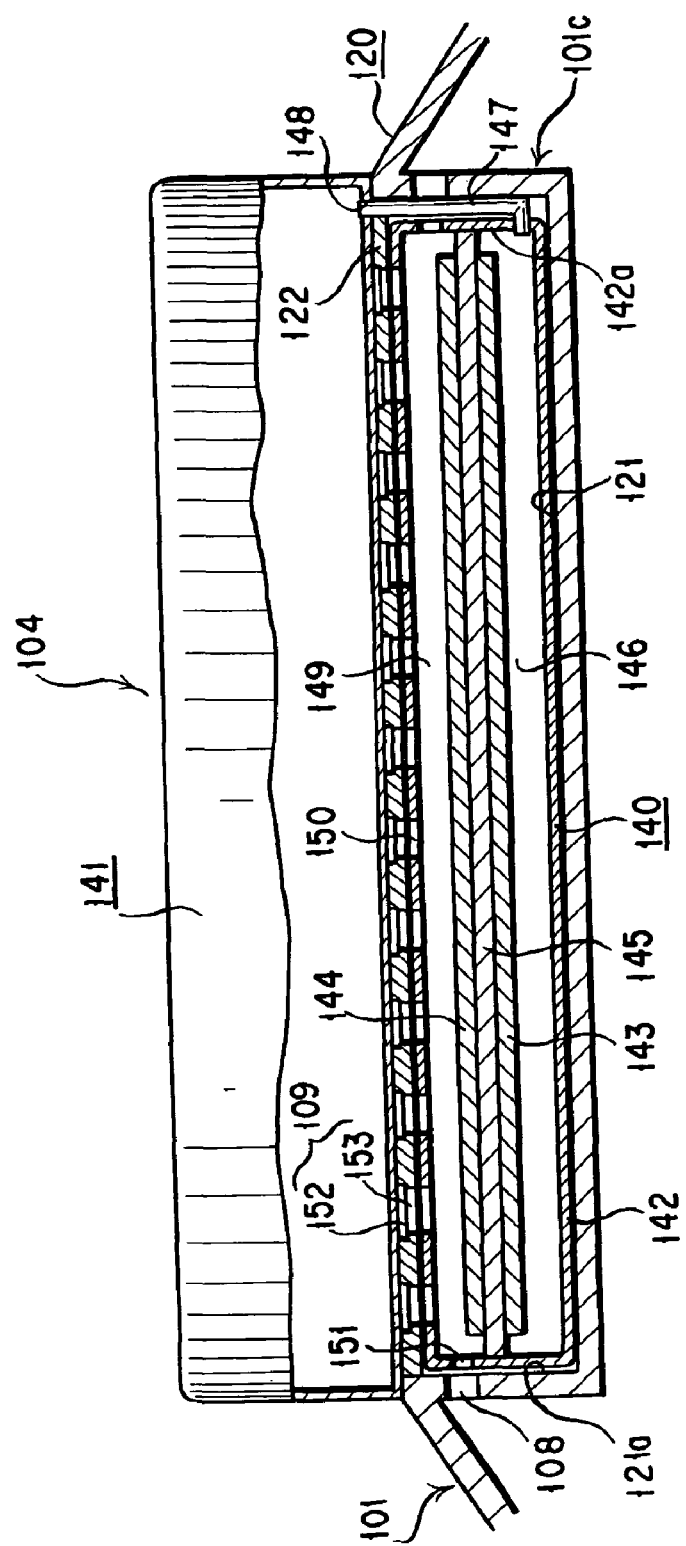
FIG. 17 is a cross sectional view of a fuel cell mounting part illustrating an eighth form of implementation of the present invention.

For example, in an eighth form of implementation as shown in FIG. 17, the fuel supply pipe 147 is positioned to extend between a side wall 142a of the receptacle 142 and an inner side face 121a of the recess section 121 and has one end penetrating through the side wall 142a of the receptacle 142 into the fuel retention space 146 and the other end projection upwards through the lid 122 and fitted with the fuel supply port 148 of the fuel tank 141.

The fuel tank 141 shown in FIG. 17 is designed to cover an entire surface of the lid 122 and for this reason, the top of the lid 122 is formed with recesses 152 below which holes 153 are formed in the receptacle 142 so that the open air is allowed to flow into between the lower surface of the fuel tank 152 and the holes 153 and then into the receptacle 142 with the recesses 152 and the holes 153 together constituting the inflow ports 109 mentioned above.

In this case, the fuel tank 141 may also be made smaller in width than the lid 122 so that it covers only a portion of the lid 122.

Figure 18:
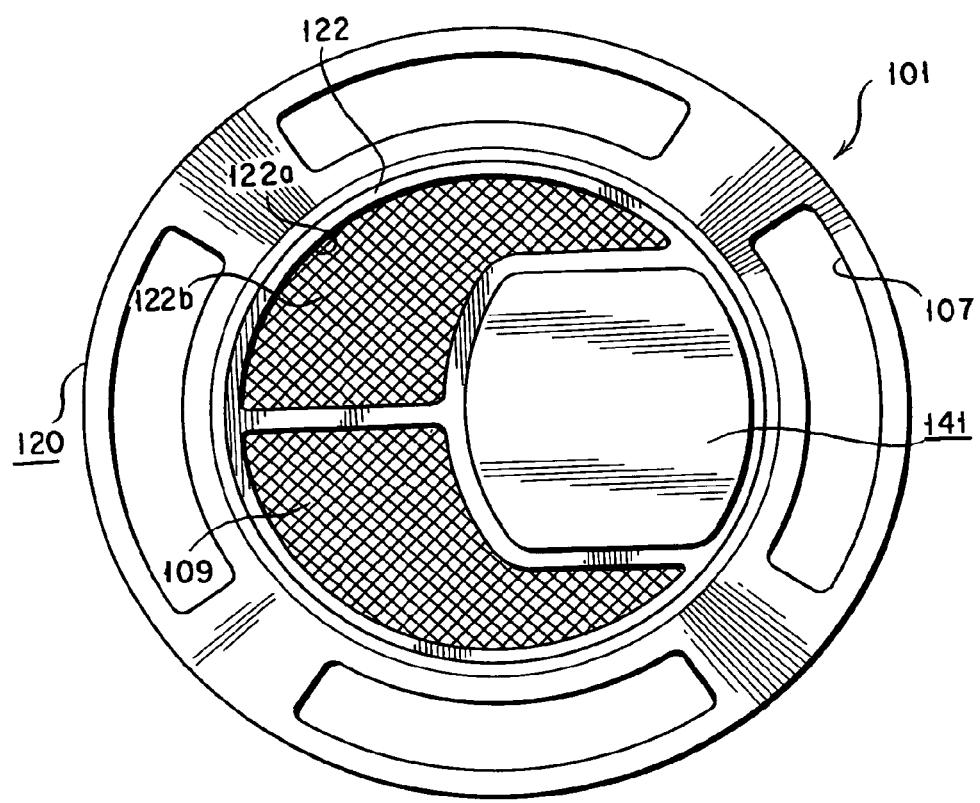
FIG. 18 is a cross sectional view of a blower type chemical diffusing apparatus illustrating a ninth form of implementation of the present invention.
Figure 19:
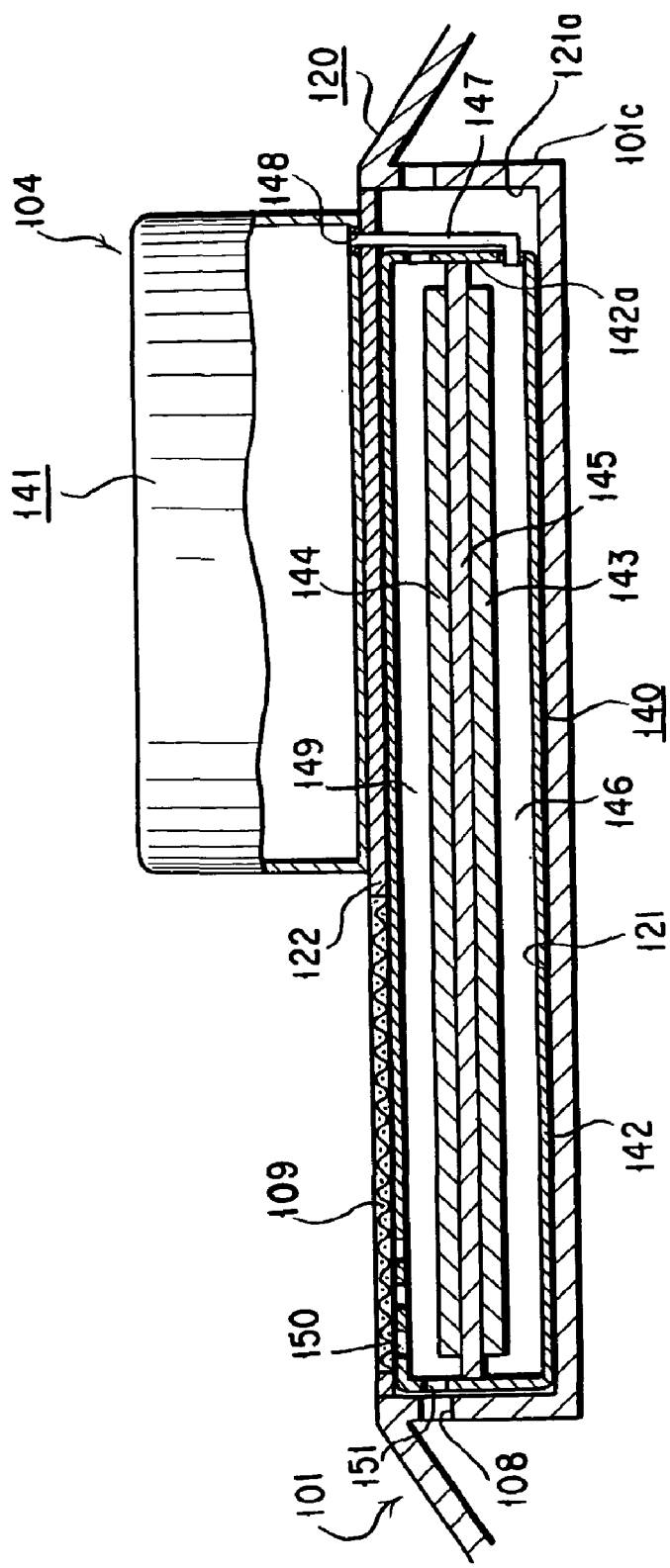
FIG. 19 is an enlarged cross sectional view of a fuel cell mounting part in the apparatus shown in FIG. 18.

For example, in a ninth form of implementation as shown in FIGS. 18 and 19, the fuel tank 141 is smaller in width than the lid 122 and is mounted on the lid 122 closer to its one end so that inflow ports 109 may be formed in the lid 122 closer to its other end.

While these forms of implementation the cell body 140 and the fuel tank 141 are each shown to be circular in planar configuration, they may, for example, be square or rectangular in planar configuration.

Also, while the cell body 140 is shown so that the negative electrode 143 lies lower and the positive electrode 144 lies upper, they may be positioned in any suitable way.

Figure 20:
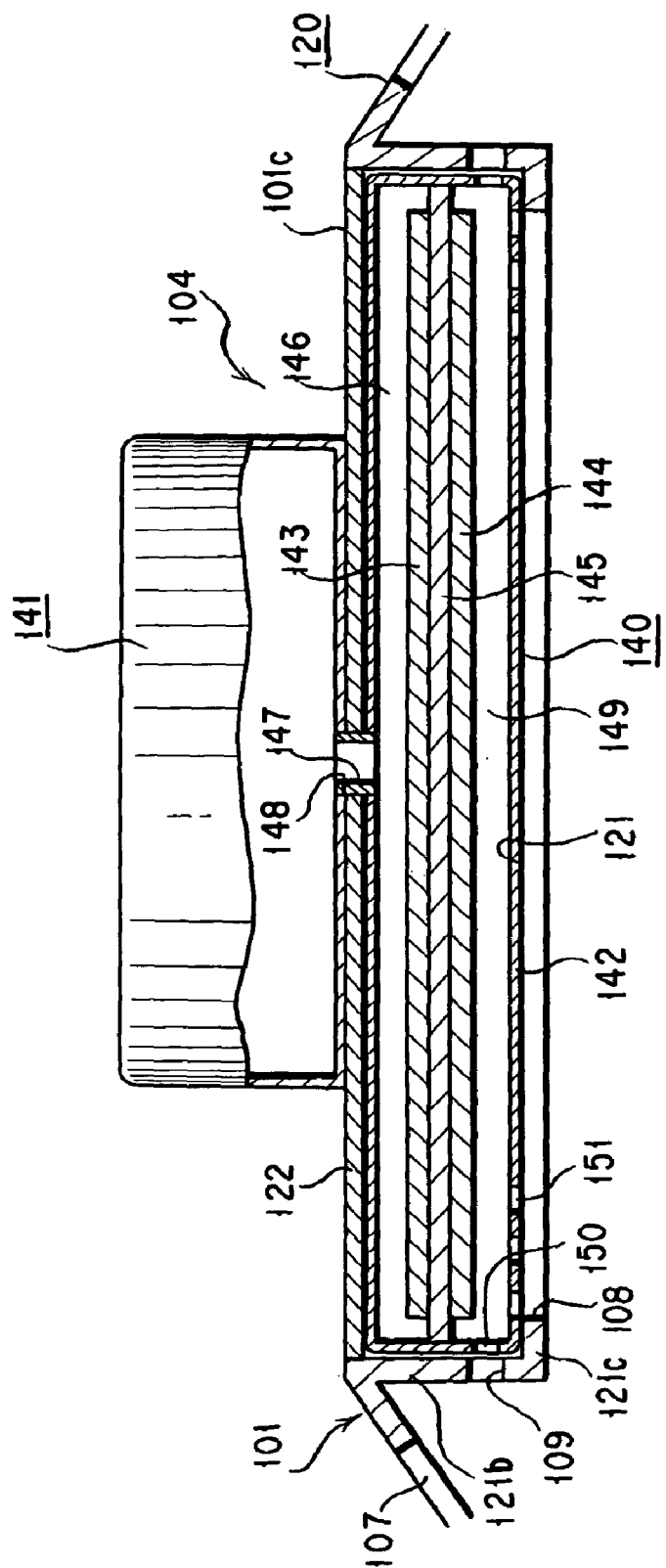
FIG. 20 is an enlarged cross sectional view of a fuel cell mounting part illustrating a tenth form of implementation of the present invention.

For example, in a tenth form of implementation as shown in FIG. 20, the negative and positive electrodes 143 and 144 are positioned to lie upper and lower, respectively.

In this case, since the fuel retention space 146 lies upper and the water forming space 149 in which product water is produced lies lower in the cell receptacle 142, the fuel supply pipe 147 connected to the fuel tank 141 is passed through the lid 122 and the upper wall of the receptacle 142 into the fuel retention space 146.

Also, in this form of implementation, the recess section 121 is formed in its side wall 121b with inflow ports 109 and in its lower wall with an outflow port 108 so that air introduced through the main inflow port 107 flows past the inflow ports 109, inlet ports 150, the water forming space 149, outlet ports 151 and the outflow port 108.

In connection with the seventh to tenth forms of implementation of the present invention mentioned above, it should be noted that the apparatus body 101 may be embodied in various forms including making the main frame 110 and the fuel cell mounting frame 120 separately from or integrally with each other, making the fuel cell 104 and/or the fuel tank 141 detachable for reattachment, and making the main frame 110 (including the cell body) and the fuel tank 141 separately from each other. Further, the power magnitude of the fuel cell 104, the rate of airflow in and from the main frame 110, the quantitative scale of chemical for diffusion and the form of the apparatus such as if it is of portable or fixed type can be embodied variously, depending on particular purposes and applications of the apparatus.

The fuel cell 104, especially the cell body 140, is positioned upstream of the chemical retainer 103 in the air current passage in which air is forced to flow by the air blower 102 in the apparatus body 101. This is desirable because the fuel cell 104 then without being exposed to chemical is prevented from contamination and thereby made trouble-free.

Also, in mounting the fuel cell 104, there is no particular limitation in the relative position of the cell body 140 to the fuel tank 141 at least if it is ensured that the negative and positive electrodes 143 and 144 are supplied, respectively, with amounts of fuel and of air which are sufficient not to hinder power generation by the fuel cell 104 and that air is forced to flow over the cell body 140 (the positive electrode).

There is also no particular limitation in the shape of the blower type chemical diffusing apparatus of the invention, the apparatus body 101 or the main frame 110; it may illustratively be circular, square, triangular or polygonal.

There is also no particular limitation in the shape of the fuel cell mounting frame 120; illustratively it may be circular, square, triangular or polygonal. And, neither is there in the shape of the fuel tank 41; it may illustratively be circular or square. Also, they may have different shapes which may be combined.

The fuel cell mounting frame 120 may be provided with a chamber or chambers in which the cell body 140 and/or the fuel tank 141 is/are mounted and may also have either or both of them mounted directly therein without such chamber or chambers formed.

There is also no particular limitation in the shape of each of the air inlet and outlet ports to the cell body 140 (positive electrode) unless its function is impeded; it may illustratively be in the form of a pore, slit, mesh or honeycomb. Neither is there in the shape or size of such a port unless it hinders inflow or outflow of air into or from the fuel cell 104.

Mention is next made of an eleventh form of implementation of the present invention.

Figure 21:
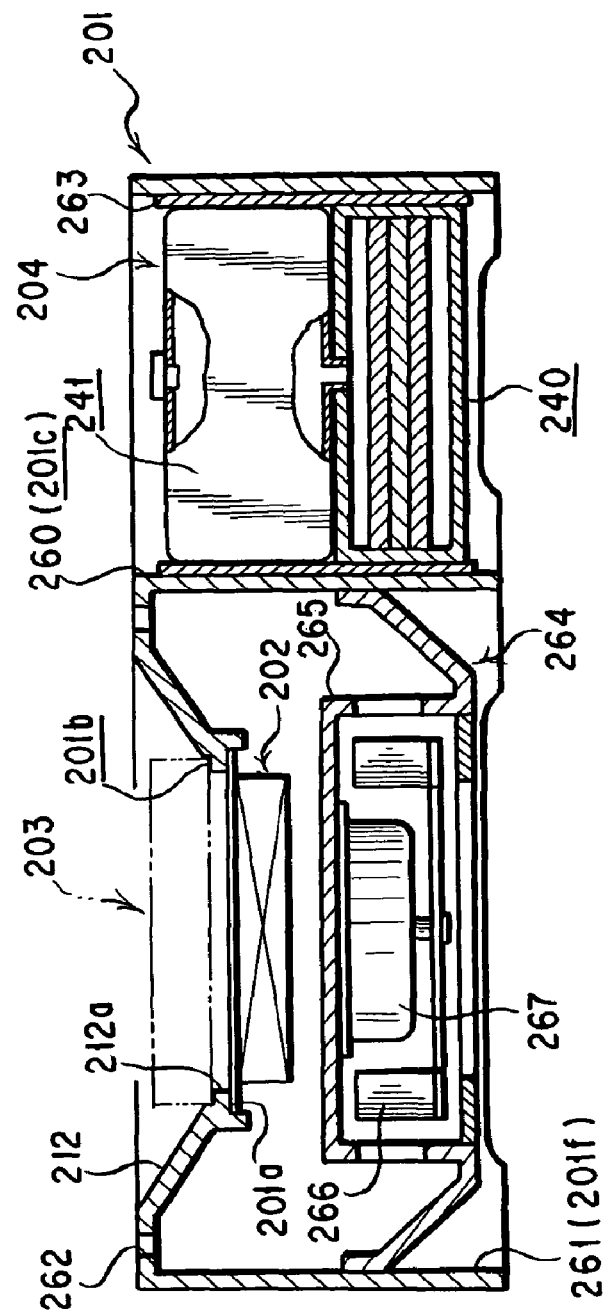
FIG. 21 is a cross sectional view of a blower type chemical diffusing apparatus illustrating an eleventh form of implementation of the present invention.
Figure 22:
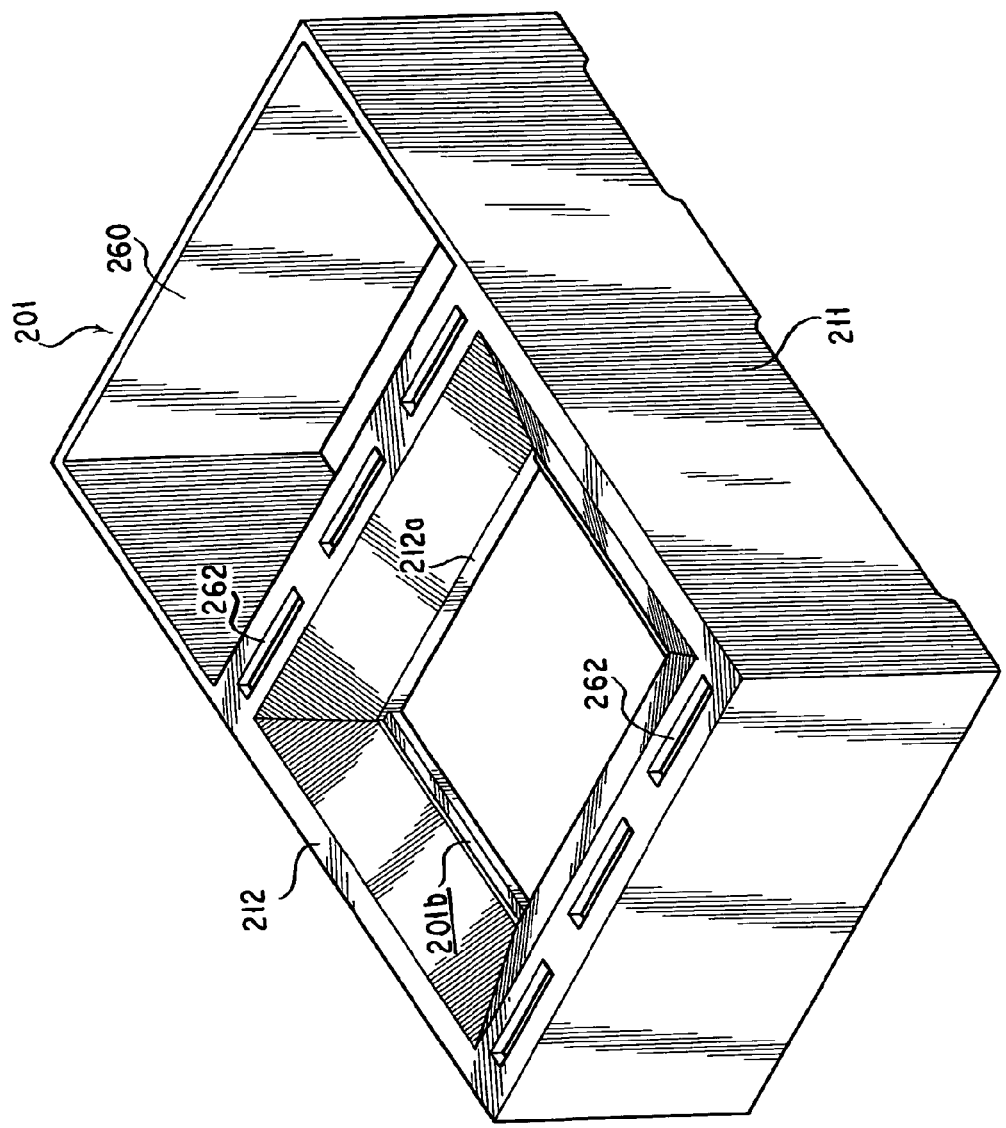
FIG. 22 is a perspective view of an apparatus body of the apparatus shown in FIG. 21.
Figure 23:
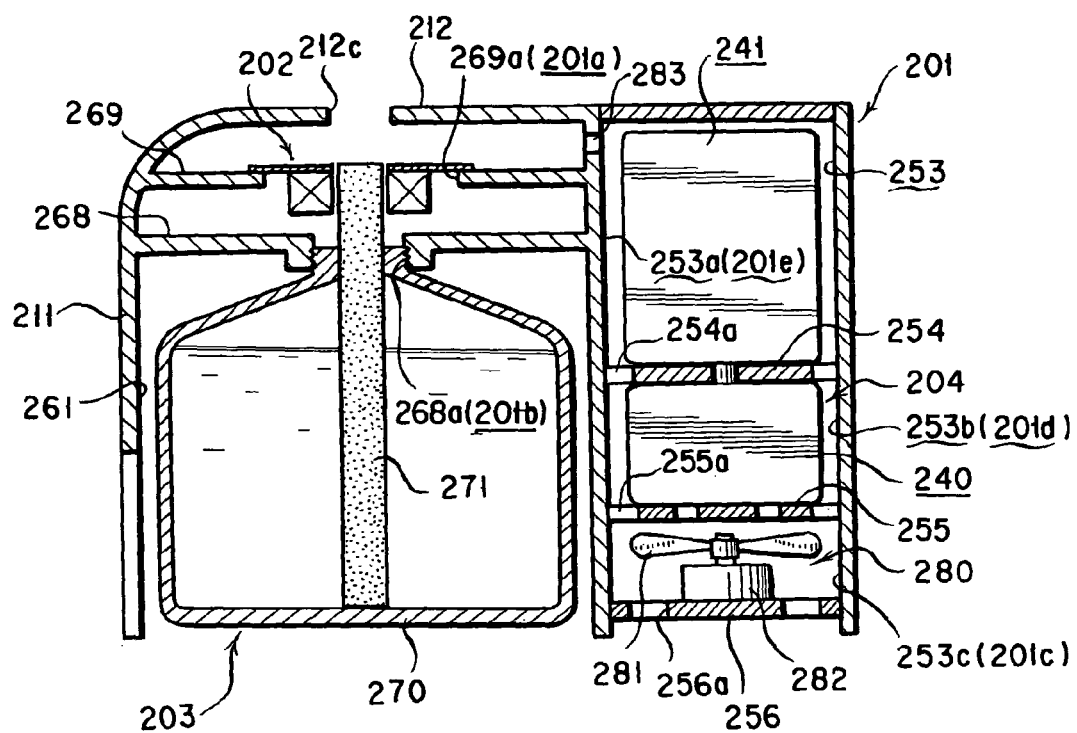
FIG. 23 is a cross sectional view of a chemical volatilizing apparatus illustrating a twelfth form of implementation of the present invention.

As shown in FIGS. 21 and 22, the apparatus comprises an apparatus body 201, and a heat emitter 202, a chemical retainer 203 and a fuel cell 204 included in the apparatus body 210. The heat emitter 202 is powered by the fuel cell 204 as its power supply to emit heat whereby the chemical retainer 203 is heated to volatilize chemical. The apparatus also includes an air blower 264 which is used to promote diffusion of volatilizing chemical into the atmosphere.

The heat emitter 202 is in the form of a plate that is larger than an opening 212a formed in a top plate 212 and is fastened to the top plate 212 underneath the opening 212a (at an emitter mounting section 201a) so as to close the opening 212a therewith.

To mention an example of the heat emitter 202 specifically, a heat emitting element made of PTC thermistor is received in an insulating case to which a planar radiator plate is joined and which is sealed with a cover. This PTC thermistor (positive thermistor) when reaching a certain temperature decreases its current and when reduced in temperature increases its current automatically, thus functioning as a constant-temperature heat emitter, and is known to be high in temperature stability and safety.

The apparatus body 201 is formed at its one side with a hollow 260 that is top and bottom open to provide a fuel cell accommodating section 201c.

The apparatus body 201 is formed at its other side with a bottom open recess 261 to provide a blower mounting section 201f.

At the other side of the apparatus body 201, the top plate 212 formed with the opening 212a provides both the emitter mounting section 201a and a chemical retainer mounting section 201b. The top plate 212 is formed around the opening 212a (around the chemical retainer mounting section 201b) is formed with an air blast portion comprising, for example, a plurality of holes each in the form of a slit.

The hollow 260 in the apparatus body 201 is fitted with a cylinder 263 in which a cell body 240 and a fuel tank 241 have been mounted.

Mounted in the bottom open recess 261 of the apparatus body 210 is an air blower 264.

The air blower 264 comprises a fan 266 and a motor 267 which are received in a housing 265 whereby rotating the fan 266 with the motor 267 produces air flows upwards through the air blast sections 262. The motor 267 is powered by a fuel cell as its power supply.

With the apparatus so constructed, air flows upwards through the sir blast sections 262 act to promote the diffusion of chemical volatilizing from the chemical retainer 203 into the atmosphere.

By the way, it is also possible to position the air blower 264 upwards apart from the chemical retainer 203 so that volatilizing chemical may be entrained in a drawn air current and emitted therewith into the atmosphere.

Mention is next made of a twelfth form of implementation of the present invention with reference to FIG. 23.

This is a form of implementation in which the chemical retainer 203 is of liquid chemical bottle type.

The apparatus body 201 is formed at its one side with a hollow 253 which is divided with cross plates 254 and 255 into an upper hollow 253*a*, an intermediate hollow 253*b* and a lower hollow 253*c*, to constitute a fuel tank accommodating section 201*e*, a cell body accommodating section 201*d* and a blower accommodating section 201*c*, respectively.

A fuel cell 204 is mounted at the one side of the apparatus body 201. To wit, a fuel tank 241 and a cell body 240 of the fuel cell 204 are accommodated in the upper hollow 253*a* and the intermediate hollow 253*b*, respectively.

The apparatus body 201 is formed at its other side with a bottom open recess 261 having a first and a second cross plate 268 and 269.

The first and second cross plates 268 and 269 are formed with a threaded hole 268*a* and a hole 269*a* to constitute a chemical retainer mounting section 201*b* and a heat emitter mounting section 201*a*, respectively.

A top plate 212 is formed with an opening 212*c* through which chemical is to volatilize and which is vertically continuous with the hole 269*a* and the threaded hole 268*a*.

The chemical retainer 203 is of a liquid chemical bottle type in which a liquid absorbing wick or strip 271 is immersed in a chemical containing bottle 270 and the chemical retainer 203 has a threaded part at its mouth which is screwed into the threaded hole 268*a* for its mounting.

The heat emitter 202 is in the form of a ring and is mounted on the cross plate 269 above the hole 269*a*.

An upper end of the liquid absorbing strip 271 is passed through the ring-shaped heat emitter 202 so that when heated it can volatilize liquid chemical absorbed therein.

The air blower 280 is mounted on a bottom plate 256 secured to a lower part of the apparatus body 201 and is thereby securely disposed in the lower hollow 253*c*. The air blower 280 comprises a fan 281 and a motor 282 which is powered by the fuel cell 204 as its power supply.

The bottom plate 256, the cross plate 255 and the cross plate 254 are formed with suction ports 256*a*, and airflow ports 255*a* and 254*a*, respectively. Further, a partition between the upper hollow 253*a* and a region of the chemical volatilizing opening 212*c* is formed with an air blast port or ports 283.

With the apparatus so constructed, rotating the fan 281 with the motor 282 in the air blower 280 causes air to be drawn through the suction ports 256*a* and then past the airflow ports 255*a* and 254*a* to be blown out through the air blast port or ports 283 and further through the chemical volatilizing opening 212*c*, then emanating into the atmosphere. Diffusion of chemical volatilizing from the chemical retainer is thus promoted by air forced to be flowing from the blast ports 256*a* upwards through the chemical volatilizing opening 212*c*.

Further, volatilization of chemical is promoted by the fact that the heat generated in the cell body 240 is entrained in air forced to flow from the suction ports 256a and through the air blast port 283.

For the heat emitter 202 utilized in the eleventh and twelfth forms of implementation of the invention, use may be made illustratively of a resistance heater (cement resistor, metal oxide film resistor, carbon film resistor, nichrome wire or the like), or a heater using a semiconductor (PTC).

Also, for the heat emitting element, use may be made, as desired, of a PTC thermistor, a tableted and sintered resistor containing a semiconductor or conductive carbon as a main constituent, or a resistor having conductive carbon kneaded in resin. A Peltier element (thermoelectric semiconductor) may also be used.

Also, the heating temperature of the heat emitter 202 is not limited to but may be set depending on the types of the emitter and fuel cell used and may be selected in accordance with the purpose and application of the apparatus.

When made portable or small-sized, the apparatus is high in handling safety if the heat emitter is used at a reduced temperature. Then, it can also limit power consumption conveniently with a fuel cell reduced in size.

The heating temperature of the heat emitter should, for example, have a upper limit of 100° C. and a lower limit of 40° C.

In the chemical retainer 203 used in the present invention, the chemical impregnated body 230 may be composed of a material illustratively such as paper (pulp, linter, synthetic paper, etc), wood (saw dust, etc), ceramic, fiber (chemical fiber, glass fiber, carbon fiber, etc), natural fiber (cotton, wool, silk, flax, etc), resin (polyethylene, polypropylene, rayon, viscose, highly oil adsorptive polymer, etc), nonwoven fabric, or dry material such as of natural plant.

The chemical impregnated body 230 may illustratively be in the form of a sheet, net, honeycomb, drain board, lattice, flocculation, particles or a mat. It may also be in the form of a porous bag or receptacle that may be circular, square, rectangular or polygonal in shape.

Also, when the heat emitter is heated at a low heating temperature (e. g., 100° C. or less), the chemical retainer should desirable be made of a material high in air permeability or a formed body thereof, among the materials mentioned above. For example, to facilitate flow of warm air through the chemical retainer, the body should preferably be such as of nonwoven fabric and such as in the form of a net or honeycomb, or have a large number of pores.

Also, to increase the amount of impregnation of chemical, a measure such as pleating or folding a nonwoven fabric may be taken.

Also, in the chemical retainer 203 used in the present invention, liquid chemical may be an oily liquid chemical in which a chemical or an active ingredient to be described later is dissolved in a suitable solvent, for example, a petroleum solvent such as normal paraffin, iso-paraffin or naphthene hydrocarbon (liquid paraffin), or any other liquid chemical, such an aqueous liquid chemical, having the chemical solubilized with water, a surface active agent or alcohol, etc.

Mention is next made of a thirteen form of implementation of the present invention.

Figure 24:
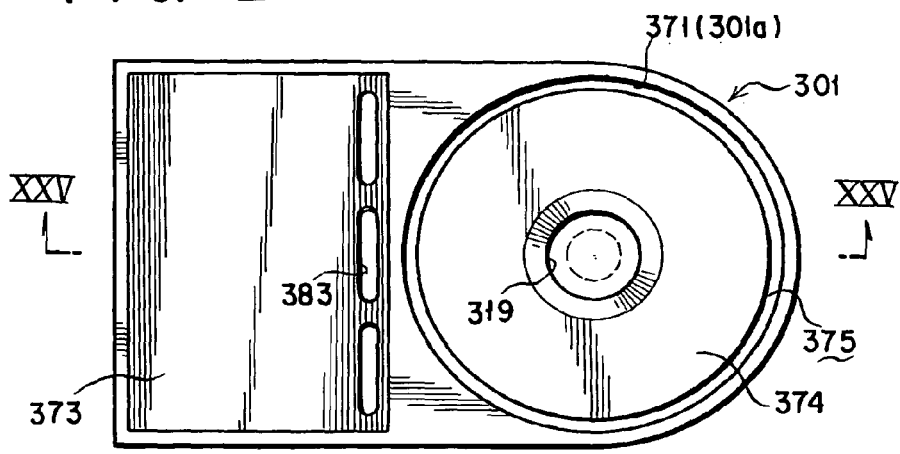
FIG. 24 is a plan view of a blower type chemical diffusing apparatus illustrating a thirteenth form of implementation of the present invention.
Figure 25:
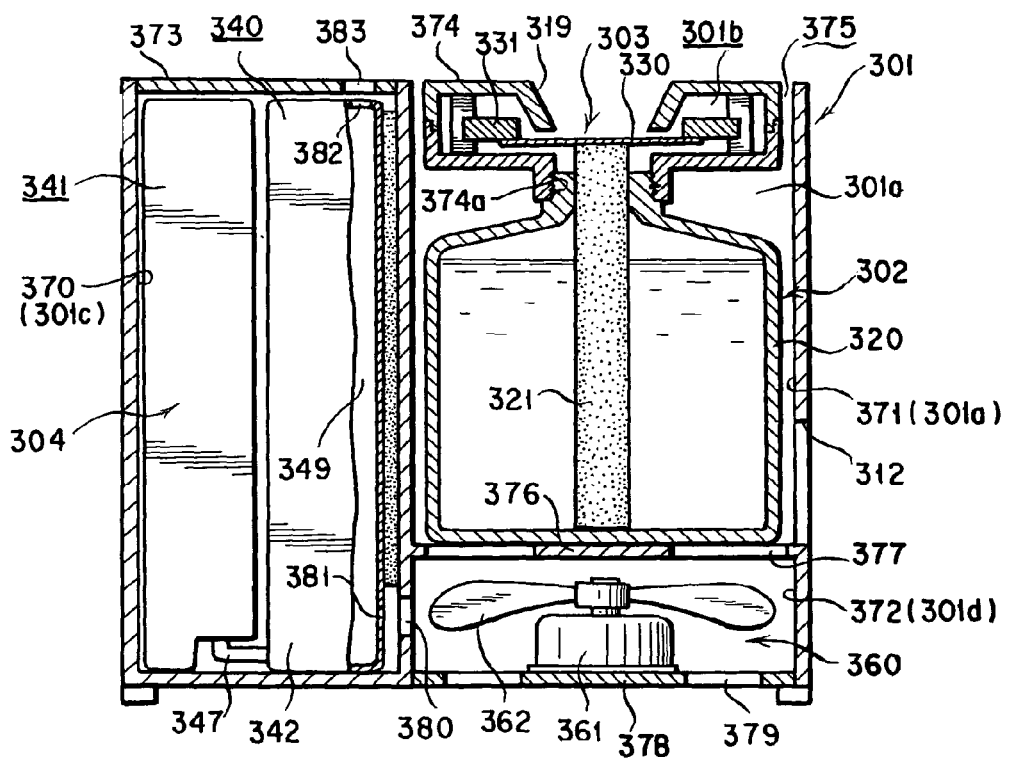
FIG. 25 is a cross sectional view taken along the line XXV-XXV in FIG. 24.

As shown in FIGS. 24 and 25, a chemical receptacle 302, an ultrasonic generating mechanism 303 and a fuel cell 304 are mounted in an apparatus body 301.

The ultrasonic generating mechanism 303 is powered by the fuel cell 304 as its power supply to generate ultrasonic waves, thereby atomizing liquid chemical (chemical in the form of liquid) in the chemical receptacle 302.

Mention is made of the specific configurations of these members.

The apparatus body 301 includes a chemical receptacle accommodating section 301a, an ultrasonic generating mechanism accommodating section 301b and a fuel cell accommodating section 301c.

In FIGS. 24 and 25, the apparatus body 301 is shown formed at one of its right and left hand sides with a first top open recess 370 that is rectangular in section, and at the other of its right and left hand sides with a second top open recess 371 and a hollow 372 each of which is circular in section. The first top open recess 370 has its opening adapted to be opened and closed with a lid 373 and constitutes the fuel cell accommodating section 301c.

The second top open recess 371 and the hollow 372 are formed to constitute the chemical receptacle accommodating section 301a and a blower accommodating section 301d, respectively.

The chemical receptacle 302 has a liquid absorbing wick or strip 321 inserted into the chemical containing receptacle body 320 which is screwed into a threaded hole 374a of the hollow 374 and thereby removably attached thereto. The liquid absorbent strip 321 is passed through the threaded hole 374a into the ultrasonic generating mechanism accommodating section 301b and has its upper end preferably facing an spray nozzle 319 to be described later.

The receptacle body 320 consists of a transparent receptacle that allows visually checking an amount of chemical remaining therein. For example, the top open recess 371 of the apparatus body 301 is formed in its peripheral wall with a cutout 312 through which an amount of liquid chemical can be visually checked so that when the liquid chemical becomes depleted, the receptacle body 320 may be replaced.

The ultrasonic generating mechanism 303 comprises a diaphragm 330 and an oscillator 331, e. g., a piezoelectric oscillator 331 which is connected to a piezoelectric oscillating circuit (not shown) in which it is powered by the fuel cell 304 to produce ultrasonic waves which are transmitted to the diaphragm 330 so that liquid chemical supplied from the receptacle body 320 through the liquid absorbing strip 321 to the diagram 330 can be atomized and sprayed through the spray nozzle 319 into the atmosphere. Here, the liquid absorbent strip 321 is one example only of means for feeding the diaphragm 330 with liquid chemical which may be other than a liquid absorbent strip and may, for example, be by dropping a liquid chemical on the diaphragm.

The fuel cell 304 comprises a cell body 340 and a fuel tank 341.

The cell body 340 and the fuel tank 341 are mounted in the fuel cell mounting section 301 and can be mounted and dismounted upon removing the lid 373.

Mounted below the apparatus body 301 is an air blower 360 whose blast air is discharged around the spray nozzle 319 and then upwards, thereby to promote spraying of atomized chemical.

Concurrently, a portion of the blast air from the blower 360 is directed through a space in which product water is produced during the power generation by the cell body 340, and then is discharged into the atmosphere.

This allows such product water produced during the power generation to be efficiently vaporized and expelled into the outside. The air blower 360 is driven by the fuel cell 304 as its power supply.

Above the receptacle body 320 of the chemical receptacle 302 there is mounted a hollow 374 that is circular in section, which constitutes the ultrasonic generating mechanism accommodating section 301b and which has the ultrasonic generating mechanism 303 mounted therein and is formed at its top with the spray nozzle 319.

Defined with the second top open recess 371, the outer face of the receptacle body 374 and the hollow 374 there is formed an annular space 375 that is continuous vertically.

A partition wall 376 that partitions the hollow 372 and the second top open recess 371 is formed with first discharge ports 377 that communicate with the continuous annular space 375.

In the hollow 372 the air blower 360 is mounted on its bottom plate 378 which is formed with suction ports 379.

In the air blower 360, a fan 362 is rotated by a motor 361 to cause air to be drawn through the suction ports 379, to flow through the discharge ports 377 and to be discharged through the space 375 into the outside.

This produces air flowing around the spray nozzle 319 and then upwards to promote spraying of atomized chemical.

The hollow 372 communicates with the first top open recess 370 via communicating port or ports 380 which in turn communicate with the water forming space 349 via inflow ports 381 formed in a vessel 342 of the cell body 340, and the space 349 communicates with the outside via an outflow port or ports 382 formed in the vessel 342 and via discharge ports 383 formed in the lid 373.

With the apparatus so constructed, rotating the fan 362 causes air to flow past the communicating port 380, the inflow ports 381, the space 349, the outflow port 382 and the discharge ports 383, thereby permitting product water produced during the power generation to be efficiently vaporized and expelled into the outside as mentioned above.

The abovementioned means for spraying liquid chemical upon atomization by utilizing ultrasonic waves is not limited to a piezoelectric atomizer as described but may be any of the particular means described below.

First, it may be one in which a diaphragm adapted to vibrate ultrasonically is disposed in liquid chemical to atomize liquid chemical; specifically it comprises liquid chemical, an atomizing bath and a diaphragm disposed in the atomizing bath wherein the diaphragm disposed in the atomizing bath when a voltage of a selected frequency is applied across a pair of electrodes formed on its opposite sides brings about magnetostrictive vibrations and outputs ultrasonic vibrations which are imparted to liquid chemical, thereby atomizing liquid chemical.

Second, it may be one in which a diaphragm adapted to vibrate ultrasonically is disposed in an atomizing cylinder to draw up and atomize liquid chemical in the atomizing cylinder; specifically it may use an ultrasonic pump or utilize an ultrasonic transducer wherein it comprises a mechanism of an piezoelectric element, a suction port and the atomizing cylinder wherein the piezoelectric element is loaded with an alternating voltage and the transducer is brought into resonance with the piezoelectric element at its natural frequency whereby power is transmitted upon enlargement to the end of the transducer to effect ultrasonic atomization.

With the compactness and handling simplicity of the apparatus taken into account, however, an atomizer of piezoelectric type or ultrasonic pump type will be preferred.

To mention of the atomizing pattern of liquid chemical atomized in the manner described above, liquid chemical may be atomized either continuously or intermittently. Intermittent atomization is effective for a particle size that is adequate to have atomized particles floating for a longer period of time and also advantageous to achieve a reduction of power consumption. It can also enhance the safety when the apparatus is used to control harmful insects using an insecticide or the like.

Active ingredients as mentioned above or below may be used either singly or in a combination.

Also, such an active ingredient or ingredients may be dissolved or mixed with a solvent to prepare a liquid chemical.

For the solvent, use may be made, for example, of aliphatic hydrocarbon, alicyclic hydrocarbon, aromatic hydrocarbon, halogenated hydrocarbon, alcohol, ester, ether and ketone.

A composition having a solvent and an active ingredient mixed with water or a composition having an active ingredient and water emulsified with a surface active agent or suspended in water may also be used as a liquid chemical.

Further, a liquid chemical may, in addition to an active ingredient and a solvent, contain an antioxidant, ultraviolet absorber, synergist, perfume, pigment, bactericide and/or fungicide, for example.

The fuel cell used in the present invention may be any of phosphoric acid type, proton-exchange membrane type, molten carbonate type, fixed oxide type and alkaline type, which are classified based on types of electrolyte included. For use as a power supply applied for blasting and diffusion of chemical, a fuel cell of proton-exchange membrane type or alkaline type should be preferred for the reasons, among others, that it is operable at a temperature close to ambient temperature, and it can be compacted in a small size.

For the fuel, use may be made of pure hydrogen (namely, hydrogen occluded alloy, hydrogen cylinder, hydrogen occluded carbon nanotube, etc), liquid fuel, natural gas, naphtha, coal gas and the others. Among others, pure hydrogen or liquid fuel should be preferred in that it is easy to handle in use and it is simple in structure and small in size. Having the advantage that it can be seen visually, the liquid fuel may be high-concentration methanol, diluted aqueous solution of methanol and may also be ethanol, propanol, dimethyl ether, ethylene glycol, etc, illustratively. In general, any fuel may be sufficient if it can furnish hydrogen for decomposition into hydrogen ions and electrons.

For the cell body, use may, of course, be made of a structure made of a plurality cells laminated, each of which comprises a separator, negative electrode, electrolyte, positive electrode and separator and the number of which is selected to meet a particular purpose as sought.

The fuel tank may be made of any material if it is satisfactory in retention stability and durability to liquid fuel. For example, synthetic resins such as polypropylene, polyethylene and polyethylene terephthalate, metals such as stainless steel, aluminum and steel, and pressure resistant glass can be listed. Also, the fuel tank may have a transparent pipe or pipes attached thereto.

The blower type chemical diffusing apparatus in which a fuel cell is used as its power supply in accordance with the present invention may not only be of the type mentioned hereinbefore in which a chemical retainer containing a volatile chemical is mounted in an air current passage traversed by air flow drawn or blasted by a fan to cause volatile chemical to be released from the chemical retainer and diffused into the outside. But it may be of the type using a fan containing such chemical. For example, such a fan may illustratively be a formed body having a chemical kneaded in resin, a fan having a chemical containing sheet attached to its outer and outer peripheral surfaces, or a fan made of an annular cartridge having chemical impregnated particles received therein.

For the fan of an air blower used in the present invention, use may be made of the centrifugal type that imparts energy to air by accelerating it radially outwards with centrifugal force, or the axial type that imparts energy to air with the lift of each blade.

The chemical retainer used in the present invention may be formed of an inorganic or organic material illustratively such as paper (pulp, linter, synthetic paper, etc), wood (saw dust, etc), ceramic, fiber (chemical fiber, glass fiber, carbon fiber, etc), natural fiber (cotton, wool, silk, flax, etc), resin (polyethylene, polypropylene, rayon, viscose, highly oil adsorptive polymer, etc), nonwoven fabric, or dry material such as of natural plant. The formed body is preferably of a shape that is larger in effective area, illustratively such as in the form of particles, lines and threads. Also, it is of a shape that is higher in air permeability, illustratively such as in the form of beads, a net, a honeycomb, a drain board or a lattice. Further, an air-permeable bag or receptacle having the abovementioned formed body stored therein is also suitable.

The chemical for use in the present invention is a volatile chemical that may be an aromatic, deodorant, bactericide, insecticide, miticide, repellant to harmful insects or animals, insecticide, insect pest growth control agent or sucking inhibitor.

Such chemicals, if used to kill insects, may be a variety of volatile insecticides so far known, of which pyrethroid, carbamate, organophosphate chemicals and so on can be listed, further of which pyrethroid chemicals can preferably be used as generally high in safety.

Further, such specific chemicals as methofluthrin, transfluthrin, empenthrin, terallethrin and profluthrin which are highly active and which in a small amount exhibit efficaciousness can desirably be used as they can make the chemical carrier thin and small and also they can in a small amount have their efficaciousness last for an extended period of time.

Further, in addition to a chemical as mentioned above, there may be added thereto where necessary a volatile adjustor (petrolatum, glycol, etc), antioxidant (BHT, BHA, etc), synergist (piperonyl butoxide, synepirin 222, etc), dissolving agent (paraffin, polyalcohol, fatty ester etc), indicator (allochroic coloring agent), ultraviolet absorber and aromatic.

What is claimed is:

1. A blower chemical diffusing apparatus comprising:
    an air blower,
    a chemical retainer, and
    a fuel cell,
    wherein the air blower, the chemical retainer and the fuel cell are included in an apparatus body, and the fuel cell is arranged to power the air blower,
    wherein when the air blower is powered by the fuel cell to be driven, the air blower causes a chemical from the chemical retainer to be emitted into an environmental atmosphere,
    wherein the fuel cell comprises a cell body and a fuel tank,
    wherein the apparatus body comprises a see-through section through which an amount of fuel remaining in the fuel tank can be visually checked,
    wherein the amount of fuel remaining in the fuel tank is correlated with at least one of an amount of the chemical and an activeness of the chemical that remains in the chemical retainer,
    wherein the see-through section comprises an indication of a timing at which the chemical retainer is to be exchanged marked at a position at which a preselected amount of fuel is to be seen to remain in the fuel tank, and
    wherein the apparatus body comprises a movable part having the chemical retainer and the fuel tank mounted thereto, the movable part being attachable to and detachable from a fixed part of the apparatus body.

2. A blower chemical diffusing apparatus as set forth in claim 1, wherein:
    the chemical retainer and the fuel tank are adapted to be supplied at around a same time with the chemical and the fuel, respectively.

3. A blower chemical diffusing apparatus as set forth in claim 1, wherein:
    the chemical retainer comprises a chemical impregnated body adapted to be heated by heat produced while the fuel cell is generating electric power to volatilize the chemical from the chemical impregnated body.

4. A blower chemical diffusing apparatus as set forth in claim 1, wherein:
    the apparatus body comprises an air flow passage through which air flows while the air blower is being driven, and the fuel cell is provided in said air flow passage.

5. A blower chemical diffusing apparatus comprising:
    a heat emitter,
    an air blower,
    a chemical retainer, and
    a fuel cell,
    wherein the heat emitter, the air blower, the chemical retainer and the fuel cell are included in an apparatus body, and the fuel cell is arranged to power the air blower,
    wherein when the heat emitter is powered by the fuel cell to emit heat, the heat emitter heats the chemical retainer to cause a chemical to volatilize from the chemical retainer,
    wherein when the air blower is powered by the fuel cell to be driven, the air blower causes the volatilizing chemical to be emitted into an environmental atmosphere,
    wherein the fuel cell comprises a cell body and a fuel tank,
    wherein the apparatus body comprises a see-through section through which an amount of fuel remaining in the fuel tank can be visually checked,
    wherein the amount of fuel remaining in the fuel tank is correlated with at least one of an amount of the chemical and an activeness of the chemical that remains in the chemical retainer,
    wherein the see-through section comprises an indication of a timing at which the chemical retainer is to be exchanged marked at a position at which a preselected amount of fuel is to be seen to remain in the fuel tank, and
    wherein the apparatus body comprises a movable part having the chemical retainer and the fuel tank mounted thereto, the movable part being attachable to and detachable from a fixed part of the apparatus body.

6. A blower chemical diffusing apparatus comprising:
    an ultrasonic generator,
    an air blower,
    a chemical retainer, and
    a fuel cell,
    wherein the ultrasonic generator, the air blower, the chemical retainer and the fuel cell are included in an apparatus body, and the fuel cell is arranged to power the air blower,
    wherein when the ultrasonic generator is powered by the fuel cell, the ultrasonic generator generates ultrasonic waves which atomize a liquid chemical from the chemical retainer,
    wherein when the air blower is powered by the fuel cell to be driven, the air blower causes the atomized chemical to be emitted into an environmental atmosphere,
    wherein the fuel cell comprises a cell body and a fuel tank,
    wherein the apparatus body comprises a see-through section through which an amount of fuel remaining in the fuel tank can be visually checked, wherein the amount of fuel remaining in the fuel tank is correlated with at least one of an amount of the chemical and an activeness of the chemical that remains in the chemical retainer, wherein the see-through section comprises an indication of a timing at which the chemical retainer is to be exchanged marked at a position at which a preselected amount of fuel is to be seen to remain in the fuel tank, and wherein the apparatus body comprises a movable part having the chemical retainer and the fuel tank mounted thereto, the movable part being attachable to and detachable from a fixed part of the apparatus body.

7. A blower chemical diffusing apparatus as set forth in claim 1, wherein:
the fuel tank is provided in one of a peripheral section and side section of the apparatus body.

8. A blower chemical diffusing apparatus as set forth in claim 5, wherein:
the fuel tank is provided in one of a peripheral section and side section of the apparatus body.

9. A blower chemical diffusing apparatus as set forth in claim 6, wherein:
the fuel tank is provided in one of a peripheral section and side section of the apparatus body.

* * * * *